US009274127B2

(12) United States Patent
Nabeshima et al.

(10) Patent No.: US 9,274,127 B2
(45) Date of Patent: Mar. 1, 2016

(54) METHOD FOR DETERMINING DEPRESSION, KIT FOR ANALYZING SEROTONIN TRANSPORTER, AND KIT FOR ANALYZING UBIQUITINATED SEROTONIN TRANSPORTER IN BLOOD

(75) Inventors: Toshitaka Nabeshima, Nagoya (JP); Akihiro Mouri, Nagoya (JP)

(73) Assignee: MEIJO UNIVERSITY, Nagoya-Shi (JP)

( * ) Notice: Subject to any disclaimer, the term of this patent is extended or adjusted under 35 U.S.C. 154(b) by 0 days.

(21) Appl. No.: 14/233,374

(22) PCT Filed: Jul. 19, 2012

(86) PCT No.: PCT/JP2012/068348
§ 371 (c)(1),
(2), (4) Date: Jan. 16, 2014

(87) PCT Pub. No.: WO2013/012038
PCT Pub. Date: Jan. 24, 2013

(65) Prior Publication Data
US 2014/0134634 A1 May 15, 2014

(30) Foreign Application Priority Data

Jul. 21, 2011 (JP) ................................. 2011-160052
Oct. 17, 2011 (JP) ................................. 2011-228055

(51) Int. Cl.
G01N 31/00 (2006.01)
G01N 33/53 (2006.01)
G01N 33/68 (2006.01)
G01N 33/94 (2006.01)
C12Q 1/68 (2006.01)

(52) U.S. Cl.
CPC .......... *G01N 33/6896* (2013.01); *C12Q 1/6881* (2013.01); *G01N 33/942* (2013.01); *G01N 2800/304* (2013.01)

(58) Field of Classification Search
CPC .............. A61K 45/06; A61K 2300/00; G01N 33/6896; C12Q 1/6883
See application file for complete search history.

(56) References Cited

U.S. PATENT DOCUMENTS

| 2005/0239110 A1 | 10/2005 | Rokutan et al. |
| 2007/0199084 A1 | 8/2007 | Blakely et al. |
| 2011/0201617 A1 | 8/2011 | Moore et al. |
| 2014/0134634 A1 | 5/2014 | Nabeshima et al. |

FOREIGN PATENT DOCUMENTS

| JP | 2005-312435 A | 11/2005 |
| JP | 2011-503125 A1 | 1/2011 |

OTHER PUBLICATIONS

Tsao et al. (Scandinavian Journal of Immunology, vol. 63, pp. 106-115, 2006).*
Lesch et al., "Primary Structure of the Human Platelet Serotonin Uptake Site: Identify with the Brain Serotonin Transporter" Journal of Neurochemistry, vol. 60, No. 6, 1993, pp. 2319-2322.
Uebelhack et al., "Brain and Platelet Serotonin Transporter in Humans—Correlation between [$^{123}$I]—ADAM SPECT and Serotonergic Measurements in Platelets", Science Direct, Neuroscience Letters 406, 2006, pp. 153-158.
Willeit et al. "Enchanced Serotonin Transporter Function During Depression in Seasonal Affective Disorder", Neuropsychopharmacology, 33, 2008 pp. 1503-1513.
Iga et ai. "Serotonin Transporter mRNA Expression in Peripheral Leukocytes of Patients with Major Depression Before and After Treatment with Paroxetine", Science Direct, Neuroscience Letters 389, 2005 pp. 12-16.
Hoyle et al. "Shared Changes in Gene Expression in Frontal Cortex of Four Genetically Modified Mouse Models of Depression", European Neuropsychopharmacology, vol. 21, 2011, pp. 3-10.
Mouri et al. "Mage-D1 Knockout Mice Express Depressive Endophenotypes Associated with Downrgulation of Serotonin Transporter Ubiquitylation" Japanese Pharmacological Society, Journal of Pharmacological Science, vol. 118, Supplement 1, Feb. 15, 2012, p. 99P and final page.
Mouri et al, Mage-D1 Regulates Expression of Depression-Like Behavior through Serotonin Transporter Ubiquitylation, The Journal of Neuroscience, Mar. 28, 2012, vol. 32, No. 13, pp. 4562-4580.
Bruss, M., Kunz, J., Lingen, B., Bonisch, H. "Chromosomal mapping of the human gene for the tricyclic antidepressant-sensitive noradrenaline transporter" Human Genetics. Apr. 1993; 91(3):278-280.
Klimek, V., Stockmeier, C., Overholser, J., Meltzer, H.Y., Kalka, S., Dilley, G., Ordway. G.A. "Reduced levels of norepinephrine transporters in the locus coeruleus in major depression" The Journal of Neuroscience. Nov. 1, 1997; 17(21):8451-8458.
Mata, S., Urbina, M., Manzano, E., Ortiz, T., Lima, L. "Noradrenaline transporter and its turnover rate are decreased in blood lymphocytes of patients with major depression" Journal of Neuroimmunology. Dec. 30, 2005; 170(1-2):134-140.

(Continued)

*Primary Examiner* — Lisa Cook
(74) *Attorney, Agent, or Firm* — Smith, Gambrell & Russell, LLP

(57) ABSTRACT

[Problem] To provide: a method for utilizing a novel marker, including a method for determining depression; and a kit for analyzing an ubiquitinated serotonin transporter.

[Solution] A method for determining depression, comprising a step of analyzing the proportion of an ubiquitinated serotonin transporter in a blood sample collected from a subject; and a kit for analyzing an ubiquitinated serotonin transporter in blood, which comprises an ubiquitinated protein collector material and an anti-serotonin transporter antibody and is used for the analysis of the proportion of an ubiquitinated serotonin transporter in a collected blood sample.

7 Claims, 10 Drawing Sheets

(56) References Cited

OTHER PUBLICATIONS

Jayanthi, L.D., Annamalai, B., Samuvel, D.J., Gether, U., Ramamoorthy, S. "Phosphorylation of the norepinephrine transporter at threonine 258 and serine 259 is linked to protein kinase C-mediated transporter internalization" The Journal of Biological Chemistry. Aug. 18, 2006;281(33)23326-23340.

Zhao, Z., Zhang, H., Bootzin, E., Millan, M.J., O'Donnell, J.M. "Association of changes in Norepinephrine and Serotonin transporter expression with the long-term behavioral effects of antidepressant drugs" Neuropsychopharmacology, Oct. 15, 2008, vol. 34, 1467-1481.

Takechi, K., Suemaru, K., Kawasaki, H., Araki, H. "Regulatory role of the dopamine and norepinephrine transporters in pentylenetetrazol-kindled mice: Association with effect of antidepressants" European Journal of Pharmacology, Dec. 30, 2011, vol. 673/Iss.1-3, 33-39.

International Search Report for PCT/JP2014/050746, dated Feb. 10, 2014 in English & Japanese.

* cited by examiner a b a b

SEQUENCE LISTING

<160> NUMBER OF SEQ ID NOS: 8

<210> SEQ ID NO 1
<211> LENGTH: 27
<212> TYPE: DNA
<213> ORGANISM: Artificial
<220> FEATURE:
<223> OTHER INFORMATION: HA sequence tag

<400> SEQUENCE: 1
tacccctacg acgtgcccga ctacgcc                27

<210> SEQ ID NO 2
<211> LENGTH: 24
<212> TYPE: DNA
<213> ORGANISM: Artificial
<220> FEATURE:
<223> OTHER INFORMATION: SERT gene primer 1

<400> SEQUENCE: 2
ggatttcctc ctgtctgtca ttgg                   24

<210> SEQ ID NO 3
<211> LENGTH: 25
<212> TYPE: DNA
<213> ORGANISM: Artificial
<220> FEATURE:
<223> OTHER INFORMATION: SERT gene primer 2

<400> SEQUENCE: 3
ccaccattct ggtagcatat gtagg                  25

<210> SEQ ID NO 4
<211> LENGTH: 24
<212> TYPE: DNA
<213> ORGANISM: Artificial
<220> FEATURE:
<223> OTHER INFORMATION: Taqman probe

<400> SEQUENCE: 4
ccgtggacct gggcaacatc tggc                   24

<210> SEQ ID NO 5
<211> LENGTH: 20
<212> TYPE: DNA
<213> ORGANISM: Artificial
<220> FEATURE:
<223> OTHER INFORMATION: control primer 1

<400> SEQUENCE: 5
gggctatgct ctccctcacg                        20

```
<210> SEQ ID NO 6
<211> LENGTH: 21
<212> TYPE: DNA
<213> ORGANISM: Artificial
<220> FEATURE:
<223> OTHER INFORMATION: control primer 2

<400> SEQUENCE: 6
gtcacgcacg atttccctct c                                            21

<210> SEQ ID NO 7
<211> LENGTH: 22
<212> TYPE: DNA
<213> ORGANISM: Artificial
<220> FEATURE:
<223> OTHER INFORMATION: Taqman probe

<400> SEQUENCE: 7
cctgcgtctg gacctggctg gc                                           22

<210> SEQ ID NO 8
<211> LENGTH: 9
<212> TYPE: PRT
<213> ORGANISM: Artificial
<220> FEATURE:
<223> OTHER INFORMATION: HA sequence tag

<400> SEQUENCE: 8

Tyr Pro Tyr Asp Val Pro Asp Tyr Ala
1               5
```

METHOD FOR DETERMINING DEPRESSION, KIT FOR ANALYZING SEROTONIN TRANSPORTER, AND KIT FOR ANALYZING UBIQUITINATED SEROTONIN TRANSPORTER IN BLOOD

TECHNICAL FIELD

The present invention relates to a method for utilizing a novel marker, a kit for analyzing a serotonin transporter, and a kit for analyzing an ubiquitinated serotonin transporter.

BACKGROUND ART

Depression is a disease showing symptoms such as chronic depressed mood, disappearance of interest and delight, marked change in the body weight, insomnia or hypersomnia, mental decay, psychomotor agitation or retardation, feeling of worthlessness and guilty, decay of thought and concentration, and suicidal ideation, according to Diagnostic and Statistical Manual of Mental Disorders: DSM-4 by American Psychiatric Association.

In the clinical condition of depression, the monoamine hypothesis related with the decrease in the neural transmission of serotonin, noradrenaline, and dopamine is proposed. For serotonin, in a healthy subject, a sufficient amount of serotonin is released from the presynaptic nerve terminal to the synaptic cleft, and the serotonin receptor present in the postsynaptic nerve terminal receives the serotonin, whereby signal transduction is achieved, and the serotonin transporter removes excessive serotonin from the synaptic cleft, and serotonin is released again from the presynaptic nerve terminal to the synaptic cleft. In a patient with depression, it is considered that the amount of serotonin released from the presynaptic nerve terminal is insufficient, so that the postsynaptic nerve terminal cannot receive a sufficient amount of serotonin. More specifically, in a patient with depression, the serotonin amount in the synaptic cleft is likely deficient.

Based on the monoamine hypothesis, there are a diagnosis of depression using serotonin as the index, and antidepressants including a selective serotonin reuptake inhibitor such as sertraline (SSRI) as an active ingredient.

It has been reported that the expression of serotonin transporter in the central nervous system is related with the expression in platelets and leucocytes. Based on the fact that the serotonin transporter in platelets and leucocytes containing lymphocytes has many common properties with the serotonin transporter in the central serotonin nerves, the serotonin transporter in the platelets and leucocytes containing lymphocytes obtained from the peripheral blood is studied as a biological marker of depression. It has been also reported that the serotonin transporter in platelets has the same gene sequence with that revealed at the serotoninergic neuronal system. It has been also reported that the change in the expression of the serotonin transporter is related with the function in the central nervous system and psychiatric symptoms such as seasonal affective disorder. However, the mechanism supporting the relationship is still unknown.

In addition, many depression model animals are proposed for development of antidepressants for treating serotonin-related depression. These model animals show the depression-like behavior, which is disappeared by the administration of serotonin or the inhibition of serotonin reuptake from the synaptic cleft. Accordingly, the depression model animals are used for the screening of the candidates for antidepressants.

CITATION LIST

Non-Patent Documents

Non-patent Document 1: Lesch K P, Wolozin B L, Murphy D L, Reiderer P. Primary structure of the human platelet serotonin uptake site: identity with the brain serotonin transporter. J Neurochem 1993 June; 60 (6): 2319-22. The Non-patent Document 1 discloses that the serotonin transporters in the brain and platelet are genetically and structurally identical.

Non-patent Document 2: Uebelhack R, Franke L, Herold N, Plotkin M, Amthauer H, Felix R. Brain and platelet serotonin transporter in humans-correlation between [123I]-ADAM SPECT and serotonergic measurements in platelets. Neurosci Lett. 2006 Oct. 9; 406 (3): 153-8. The Non-patent Document 2 discloses that a strong correlation of the serotonin reuptake activity in the brain and platelet is found in women.

Non-patent Document 3: Willeit M, Sitte H H, Thierry N, Michalek K, Praschak-Rieder N, Zill P, Winkler D, Brannath W, Fischer M B, Bondy B, Kasper S, Singer E A. Enhanced serotonin transporter function during depression in seasonal affective disorder. Neuropsychopharmacology. 2008 June; 33 (7): 1503-13. The Non-patent Document 3 discloses that the increase of serotonin reuptake activity is found in patients with depression in seasonal affective disorder.

Non-patent Document 4: Iga J, Ueno S, Yamauchi K, Motoki I, Tayoshi S, Ohta K, Song H, Morita K, Rokutan K, Ohmori T. Serotonin transporter mRNA expression in peripheral leukocytes of patients with major depression before and after treatment with paroxetine. Neurosci Lett. 2005 Nov. 25; 389 (1): 12-6. The Non-patent Document 4 discloses that the increase of the amount of transcription (mRNA) of the serotonin transporter gene is found in the leucocytes in the patients with depression.

DISCLOSURE OF THE INVENTION

Problems to be Solved by the Invention

Depression can be diagnosed from the behavior of the patient, and also can be physically, chemically or biologically diagnosed using a specific marker.

Conventionally, based on the above-described monoamine hypothesis, the method for diagnosing depression using the amount of serotonin in the blood as the marker was disclosed, but the accuracy was not satisfactory. More specifically, about 90% of the internal serotonin is present in the digestive tract, so that the amount of serotonin in the blood scarcely reflects the amount of serotonin in the brain.

In addition, the method for diagnosing depression by visualizing the serotonin transporter in the brain is disclosed, but the method requires an expensive apparatus and the administration of a radioactive tracer to the human body. Therefore, more simple methods for diagnosing depression are desired.

The present inventors studied the physiological function in the MAGE-D1 gene-deficient mouse. As a result of this, they have found that the MAGE-D1 gene-deficient mouse shows depression-like behavior, which is disappeared by the administration of antidepressants such as a selective serotonin reuptake inhibitor, which is effective for human, to the mouse. More specifically, for the human depression concerned with serotonin, the mouse was found to be a depression model with very high validity. In addition, the biochemical study using culture cells found an interesting fact that the MAGE-D1 protein binds with the serotonin transporter. It also found an interesting fact that the overexpression of the MAGE-D1 protein decreases the amount of the serotonin transporter. More specifically, a relationship between the amount of the MAGE-D1 protein and the amount of the serotonin transporter was found.

As a result of the further study of the depression mechanism concerned with serotonin based on the relationship found above, the present inventors have found an interesting fact that the amount of the higher molecular weight serotonin transporter is increased by the use the proteasome inhibitor in the presence of the MAGE-D1 protein. They have also identified the ubiquitinated serotonin transporter. Based on the above results using the MAGE-D1 gene-deficient mouse and cultured cells, it was considered that the molecular weight of serotonin transporter is increased by the addition of ubiquitin, degradated by proteasome, and this flow is accelerated by the MAGE-D1 protein. The MAGE-D1 gene-deficient mouse showed human depression-like behavior, which is disappeared by a human antidepressant, and thus likely has the same depression mechanism as that of human. Accordingly, it is rationally assumed that the serotonin transporter in human is also ubiquitinated, and degradated by proteasome.

Based on the above findings, the present inventors have accomplished the present invention. The present invention is intended to provide a method for utilizing a novel marker including the method for determining depression, and a kit for analyzing an ubiquitinated serotonin transporter. In addition, the present invention is also intended to provide a kit for analyzing a serotonin transporter.

Means for Solving the Problems (First Aspect)
A first aspect of the present invention for solving the above problems is a method for determining depression, including a step of analyzing the proportion of the ubiquitinated serotonin transporter in the blood sample collected from a subject.

(Second Aspect)
A second aspect of the present invention for solving the above problems is the method for determining depression of the first aspect, wherein the method for determining depression further includes a step of comparing the proportion of the ubiquitinated serotonin transporter obtained from the blood sample collected from the subject with the proportion of the ubiquitinated serotonin transporter as the control obtained from at least one healthy object.

(Third Aspect)
A third aspect of the present invention for solving the above problems is the method for determining depression of the second aspect, which determines that the subject has depression when the proportion of the ubiquitinated serotonin transporter obtained from the blood sample collected from the subject is lower than the control as a result of the comparison.

(Fourth Aspect)
A fourth aspect of the present invention for solving the above problems is a kit for analyzing an ubiquitinated serotonin transporter in the blood, including an ubiquitinated protein collector and an anti-serotonin transporter antibody, and being used for the analysis of the proportion of the ubiquitinated serotonin transporter in a collected blood sample.

(Fifth Aspect)
A fifth aspect of the present invention for solving the above problems is a kit for analyzing an ubiquitinated serotonin transporter in the blood of the fourth aspect, which is used for the diagnosis of depression.

(Sixth Aspect)
A sixth aspect of the present invention for solving the above problems is a method for determining depression including a step of analyzing the amounts of the following untreated and inhibitor-treated serotonin transporters in a blood sample collected from a subject:
(1) the amount of the untreated serotonin transporter: the amount of the serotonin transporter in the blood sample; and
(2) the amount of the inhibitor-treated serotonin transporter: the amount of the serotonin transporter in the blood sample treated with a proteasome inhibitor.

(Seventh Aspect)
A seventh aspect of the present invention for solving the above problems is the method for determining depression of the sixth aspect of the present invention, which further includes a step of analyzing the amounts of the untreated and inhibitor-treated serotonin transporters in the blood sample collected from at least one healthy subject, and further includes any one or more comparison steps of the following (3) to (5):
(3) a step of comparing the difference between the amounts of the untreated and inhibitor-treated serotonin transporters obtained from the blood sample collected from the subject (the difference between the untreated and inhibitor-treated amounts), and the difference between the untreated and inhibitor-treated amounts obtained from the blood sample collected from the healthy subject;
(4) a step of comparing the amount of the untreated serotonin transporter obtained from the blood sample collected from the subject and the amount of the untreated serotonin transporter obtained from the blood sample collected from the healthy subject; and
(5) a step of comparing the amount of the inhibitor-treated serotonin transporter obtained from the blood sample collected from the subject with the amount of the inhibitor-treated serotonin transporter obtained from the blood sample collected from the healthy subject.

(Eighth Aspect)
An eighth aspect of the present invention for solving the above problems is the method for determining depression of the seventh aspect, which determines that the subject has depression when any one or more of the following (6) to (8) is applicable:
(6) the difference between the untreated and inhibitor-treated amounts obtained from the blood sample collected from the subject is smaller than the difference between the untreated and inhibitor-treated amounts obtained from the blood sample collected from the healthy subject;
(7) the amount of the untreated serotonin transporter obtained from the blood sample collected from the subject is larger than the amount of the untreated serotonin transporter obtained from the blood sample collected from the healthy subject; and
(8) the amount of the inhibitor-treated serotonin transporter obtained from the blood sample collected from the subject is smaller than the amount of the inhibitor-treated serotonin transporter obtained from the blood sample collected from the healthy subject.

(Ninth Aspect)
A ninth aspect of the present invention for solving the above problems is the method for determining depression of the sixth aspect, which determines that the subject has depression when the amount of the inhibitor-treated serotonin transporter obtained from the blood sample collected from the subject is 1.7 times or less the amount of the untreated serotonin transporter.

(Tenth Aspect)

A tenth aspect of the present invention for solving the above problems is a kit for analyzing a serotonin transporter, including a proteasome inhibitor and an anti-serotonin transporter antibody, and being used for the analysis of the amounts of the untreated and inhibitor-treated serotonin transporters in the collected blood sample.

(Eleventh Aspect)

An eleventh aspect of the present invention for solving the above problems is the kit for analyzing a serotonin transporter of the tenth aspect, which is used for the diagnosis of depression.

Effects of the Invention (First to Third Aspects)

As described above, it is rationally assumed that a serotonin transporter in human is ubiquitinated, and degradated by proteasome.

The first to third aspects of the present invention provide, firstly, a method for determining depression utilizing the proportion of the ubiquitinated serotonin transporter which is a novel marker. According to the findings by the present inventors, if the serotonin transporter is not ubiquitinated, an excessive amount of serotonin transporter is present in the body, so that the amount of the serotonin in the synaptic cleft becomes deficient, which likely causes depression. In addition, as described above, it is reported that the expression of serotonin transporter in the central nervous system is concerned with the expression in the platelets and leucocytes containing lymphocytes.

The method of the present invention uses not the absolute amount of the ubiquitinated serotonin transporter but its proportion in the same sample. Accordingly, it is considered that the method is less influenced by the conditions of collection of the blood sample (for example, changes of the body condition, the difference of collected amounts, and the difference of the period of collection), and individual difference, and provides highly accurate results.

It is considered that the serotonin transporter is degraded by proteasome after being ubiquitinated, so that the proportion of the ubiquitinated serotonin transporter obtained from the analysis of the blood sample likely includes the information corresponding to the change in the serotonin amount not only in the stage when the blood sample is obtained but also over a time range.

Conventionally, since the degradation pathway through the ubiquitination of the serotonin transporter was unknown, it was difficult to predict the change in the amount of the serotonin in the blood. In addition, since the continuous blood collection from the subject imposes a heavy burden on the human body, the diagnosis of depression was made based on the limited information of the amount of serotonin in the blood only in the stage when the blood sample was obtained. Furthermore, as described above, about 90% of the internal serotonin is present in the digestive tract, so that it is considered that the amount of serotonin in the blood scarcely reflects the amount of serotonin in the brain.

On the other hand, when the attention is paid not to serotonin but to serotonin transporter, the serotonin transporter in platelets and leucocytes containing lymphocytes has many common properties with the serotonin transporter of the central serotonin nerves. The method of the present invention uses more abundant information with higher quality, and likely achieves higher accuracy in comparison with the method for diagnosing depression using the amount of serotonin in the blood at the time of the acquisition of the blood sample as the marker.

In addition, in comparison with the method for diagnosing depression by visualizing the serotonin transporter in the brain, the present invention does not require an expensive visualizing apparatus or the administration of a radioactive tracer to the human body, and thus is a simple diagnosis method which imposes fewer burdens to the human body.

The method for determining depression becomes more effective by comparing the proportion of the ubiquitinated serotonin transporter obtained from the blood sample of the subject and the proportion of the ubiquitinated serotonin transporter obtained from the healthy subject as the control.

In addition, the method for determining depression becomes even more effective by determining depression when the proportion of the ubiquitinated serotonin transporter obtained from the blood sample of the subject is at a lower level than the control.

(Fourth to Fifth Aspects)

The fourth to fifth aspects of the present invention provide a kit for analyzing an ubiquitinated serotonin transporter in the blood. The structure of the kit is based on the finding by the present inventors that "a serotonin transporter is ubiquitinated, and degradated by proteasome". The kit achieves particularly high effect when used for the diagnosis of depression. In addition, the kit is also useful for the use in the first to third aspects of the present invention.

(Sixth to Ninth Aspects)

Based on the findings by the present inventors, a useful method for determining depression is provided using the combination of the amounts of the serotonin transporters as the marker. The present method is based on the finding that the serotonin transporter is ubiquitinated and degradated by proteasome, and focuses attention on the behavior of the amount of the serotonin transporter. Accordingly, the method can be easily carried out without requiring the detection and measurement of the ubiquitinated serotonin transporter, while achieving the above-described effects except for the advantage of using the proportion.

In the below-described example, the expression of the serotonin transporter in the healthy subject was increased by the addition of the proteasome inhibitor. On the other hand, the increment of the expression of the serotonin transporter in the patient with depression responsive or nonresponsive to antidepressant was smaller than that in the healthy subject.

Accordingly, the method is useful for determining depression, focusing attention on the amount of the serotonin transporter in the blood sample treated or untreated with a proteasome inhibitor.

Further, the method for determining depression becomes more effective by carrying out any one or more comparison step of the above-described (3) to (5).

Further, the method for determining depression becomes more effective when depression is determined when any one or more of the above-described (6) to (8) are applicable.

If the serotonin transporter is not ubiquitinated, an excessive amount of serotonin transporter is present in the body, so that the amount of the serotonin in the synaptic cleft becomes deficient, which likely causes depression.

Accordingly, it is considered that the smaller the increase of the amount of the serotonin transporter due to the action of the proteasome inhibitor, the more excessive amount of serotonin transporter is present in the body, and the higher the possibility of having depression. Therefore, it is likely effective to focus attention on the difference between the untreated and inhibitor-treated amounts.

As a result of the comparison between a healthy subject and a patient with depression, the amount of the ubiquitinated serotonin transporter to be subjected to the subsequent degradation is likely smaller in the blood sample of the patient with depression. More specifically, the amount of the serotonin transporter is likely larger in the patient with depression. Accordingly, it is effective to focus attention on the amount of the untreated serotonin transporter.

On the other hand, the action of a proteasome inhibitor likely inhibits the degradation of the ubiquitinated serotonin transporter. Therefore, more specifically, the amount of the serotonin transporter increases in a healthy subject, but the increase found in the healthy subject is not observed in a patient with depression. Accordingly, it is also effective to focus attention on the amount of the inhibitor-treated serotonin transporter.

In addition, a method for determining depression including the comparison between the amount of the inhibitor-treated serotonin transporter and the amount of the untreated serotonin transporter obtained from the subject is also effective. This method can be easily performed because it does not require the data of healthy subjects.

(Tenth and Eleventh Aspects)

The tenth and eleventh aspects of the present invention provide a kit for analyzing a serotonin transporter. The structure of the kit is based on the finding by the present inventors that "the expression of the serotonin transporter in the healthy subject was increased by the addition of the proteasome inhibitor. On the other hand, the increase of the expression of the serotonin transporter in the patient with depression responsive or nonresponsive to antidepressant was smaller than that in the healthy subject.". The kit achieves particularly high effect when used for the diagnosis of depression. In addition, the kit is also useful for the use in the sixth to ninth aspects of the present invention.

BRIEF DESCRIPTION OF THE DRAWINGS

FIG. 7(b) shows the data suggesting that the MAGE-D1 protein binds with the serotonin transporter protein through the NHD domain.

MODE FOR CARRYING OUT THE INVENTION

Figure 1:
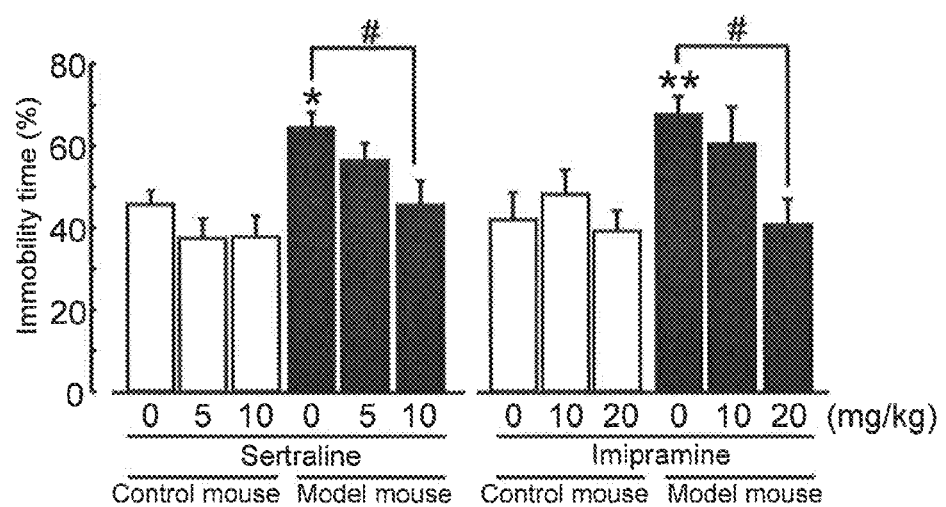
FIG. 1 shows that the depression-like behavior in the model mouse is dose-dependently relieved by human antidepressants.

The embodiments for carrying out the present invention are described below including the best embodiment.

In the present invention, ubiquitin is not particularly limited as long as it is used for protein degradation by the ubiquitin-dependent proteasome system.

In the present invention, the serotonin transporter is not particularly limited as long as it participates in serotonin uptake. The serotonin transporter is preferably a serotonin transporter expressed at the neuron forming the synaptic cleft, a serotonin transporter in platelets, a serotonin transporter in leucocytes containing lymphocytes, a serotonin transporter in digestive tract mucous membrane, a serotonin transporter in smooth muscle, and a serotonin transporter in the lung; more preferably a serotonin transporter revealed at the neuron forming the synaptic cleft, a serotonin transporter in platelets, or a serotonin transporter in leucocytes containing lymphocytes, and even more preferably a serotonin transporter in platelets, or a serotonin transporter in lymphocytes.

The serotonin transporter has genetic polymorphism including S and L genotypes, and serotonin transporters of various molecular weights can be detected from the sample prepared from, for example, platelets and leucocytes containing lymphocytes by Western blotting. In the present invention, the type of the serotonin transporter is not particularly limited.

In the present invention, the ubiquitinated serotonin transporter means a serotonin transporter combined with one or more ubiquitin. The ubiquitin is a low molecular weight protein having a molecular weight of about 8.6 kD. The ubiquitinated serotonin transporter shows a smeared and high molecular weight signal in electrophoresis or the like from its original molecular weight (about 76 kD), and is preferably an ubiquitinated serotonin transporter of 100 kD or more.

It is rationally assumed that the serotonin transporter is ubiquitinated, and degradated by proteasome also in human. Further, if the serotonin transporter is not ubiquitinated, an excessive amount of serotonin transporter is present in the body, so that the amount of the serotonin in the synaptic cleft becomes deficient, which likely causes depression. Accordingly, it is considered that the lower the proportion of the ubiquitinated serotonin transporter, the higher the possibility of having depression.

In the present invention, the proportion of the ubiquitinated serotonin transporter shows the proportion of the ubiquitinated serotonin transporter in the sample. The calculation formula for the proportion may be selected as appropriate. Examples of the formula include (1) the amount of the ubiquitinated serotonin transporter to the whole amount of the serotonin transporter, (1') the whole amount of the serotonin transporter to the amount of the ubiquitinated serotonin transporter, (2) the amount of the ubiquitinated serotonin transporter to the amount of the serotonin transporter not bound to ubiquitin, (2') the amount of the serotonin transporter not bound to ubiquitin to the amount of the ubiquitinated serotonin transporter, (3) the amount of the high molecular weight serotonin transporter to the whole amount of the serotonin transporter, (3') the whole amount of the serotonin transporter to the amount of the high molecular weight serotonin transporter, (4) the amount of the high molecular weight serotonin transporter to the amount of the serotonin transporter not bound to ubiquitin, and (4') the amount of the serotonin transporter not bound to ubiquitin to the amount of the high molecular weight serotonin transporter. For some calculation formulae, the higher the proportion, the lower the proportion of the ubiquitinated serotonin transporter. When comparing the proportion in a subject with the control obtained from a healthy subject, it is preferred that the methods for calculating the proportion of the subject and control are the same.

The embodiments of the present invention also contain the examination of the change in the proportion of the more markedly ubiquitinated serotonin transporter in the sample in which the degradation of the ubiquitinated serotonin transporter by proteasome has been inhibited by a proteasome inhibitor.

The unit used in the calculation of the proportion is not particularly limited, and may be selected as appropriate according to the method for analyzing the sample. For example, the mass, number of molecules, or signal intensity by electrophoresis including Western blotting may be used. The signal intensity by Western blotting is preferred, and the mass or number of molecules by ELISA (Enzyme-Linked ImmunoSorbent Assay), EIA (Enzyme immunoassay), RIA (Radio-ImmunoAssay) is more preferred. When the unit is the mass or other value which varies depending on the degree of ubiquitination, the amount of the ubiquitinated serotonin transporter is preferably the value excluding the ubiquitin amount. When comparing the proportions in the subject and healthy subject, the units are preferably the same.

[Method for Utilizing a Novel Marker]

The method of the present invention uses the proportion of an ubiquitinated serotonin transporter as a novel marker.

The method of the present invention includes a step of analyzing the proportion of the ubiquitinated serotonin transporter in a blood sample collected from a subject. The method is preferably a method for diagnosing depression or a method for determining depression including the above step. The method for determining depression does not include medical action by physician.

In the method of the present invention, the person who provides a blood sample under the method of the present invention is referred to as the subject. The subject is not necessarily limited to those diagnosed as depression by a physician. On the other hand, the proportion of the ubiquitinated serotonin transporter as the control is determined from a healthy subject, so that the healthy subject is not a subject.

The blood sample is not particularly limited as long as it contains an ubiquitinated serotonin transporter. As described above, it is reported that the serotonin transporter is concerned with the expression in the central nervous system and the expression in platelets and leucocytes containing lymphocytes, and it is also reported that the change in the serotonin transporter in platelets and leucocytes containing lymphocytes is related with the function in the central nervous system and psychiatric symptoms such as seasonal affective disorders. Accordingly, the blood of a subject is a favorable sample. The blood sample may be arterial or venous blood, and may be taken from any region. For example, the blood sample is preferably the peripheral blood or spinal cord fluid, and more preferably the peripheral blood. The blood sample may be collected from a subject according to a known common procedure. The blood sample may be stored according to a known common procedure.

Ubiquitination of a serotonin transporter protein may be influenced by remedy drugs such as an antidepressant or stress. Even when carrying out determination or diagnosis of depression without taking these influences into consideration, the blood may be sampled at any time. For example, it is known that the culture of leucocytes containing lymphocytes by establishment in the medium neutralizes the influences of the antidepressant in the blood and the body condition. Therefore, diagnosis or determination of depression using the proportion of the ubiquitinated serotonin transporter is considered effective irrespective of the presence or absence of administration of an antidepressant. On the other hand, when therapeutic effect of the antidepressant or stress in the subject is taken into consideration, the serotonin transporter protein in the platelets or leucocytes containing lymphocytes in the blood may be ubiquitinated without establishment.

The blood sample may be further fractionated. More specifically, the proportion of the ubiquitinated serotonin transporter in the sample fractionated from the blood sample may be analyzed. In the method of the present invention, examples of the fraction include a platelet fraction, and a leukocyte fraction containing lymphocytes, and preferred examples include a platelet fraction and a lymphocyte fraction.

The sample such as a blood sample may be a composition containing the sample. The sample may be appropriately selected according to the procedure of the analysis described below as examples.

The amount of the sample used in the method of the present invention is not particularly limited as long as the proportion of the ubiquitinated serotonin transporter can be determined. The amount may be established as appropriate according to the number of steps for determining the proportion of the ubiquitinated serotonin transporter, and the properties of the reagent and instruments used therein.

When a serotonin transporter and an ubiquitinated serotonin transporter are purified from the sample for determining the proportion of the ubiquitinated serotonin transporter, the purification method is not particularly limited. The purification method which maintains the proportion of the ubiquitinated serotonin transporter in the blood sample is preferred. Examples of appropriate methods include known methods such as fraction, precipitation, centrifugation, salting out, and immunoprecipitation using molecular weight or electric charge including chromatography or electrophoresis, and the method using an ubiquitin- or serotonin transporter-specific binding material.

The method for quantifying the serotonin transporter and ubiquitinated serotonin transporter for determining the proportion of the ubiquitinated serotonin transporter is not particularly limited. Examples of the method include immunological methods such as Western blotting, flow cytometry, ELISA, EIA, RIA, FIA, chemiluminescence immunoassay, and ECLIA. Other examples include known methods using electrophoresis or absorbance. Some quantification methods use the blood sample as it is, or requires only simple fractionation of the serotonin transporter and ubiquitinated serotonin transporter from the blood sample.

In the method of the present invention, the "healthy subject" includes those not having depression without limitation, but preferably those diagnosed not having depression by a physician, and more preferably those not exposed to psychologic stress, or those not suffering from other nerve or psychiatric disorders.

The proportion of the ubiquitinated serotonin transporter as the control is the proportion of the ubiquitinated serotonin transporter obtained from a healthy subject. The method for calculating the proportion of the ubiquitinated serotonin transporter is preferably same between the subject and healthy subject.

The sample for calculating the proportion of the ubiquitinated serotonin transporter obtained from the healthy subject as the control is preferably blood. Accordingly, the proportion is preferably determined from the blood sample of a healthy subject. The blood sample of a healthy subject may be treated in the same manner with the blood sample of a subject.

The proportion obtained from a healthy subject is used as the control. The proportion may be obtained from at least one healthy subject. However, the accuracy of the method of the present invention will be improved by using the average of the proportions obtained from plural healthy subjects.

In the method of the present invention, it is preferred that the subject is diagnosed or determined to have depression when the proportion of the ubiquitinated serotonin transporter obtained from the blood sample of the subject is at a lower level than the control. The lower level herein means the concept including that the proportion of the ubiquitinated serotonin transporter obtained from the blood sample of the subject is at least below the proportion of the ubiquitinated serotonin transporter of the control, preferably lower than the control with significant difference. According to the selection of the above-described calculation formulae, the value of the proportion of the ubiquitinated serotonin transporter obtained from the blood sample of the subject may be judged to be "lower level" even if the value is higher than the control.

When judging the low level, the proportion of the ubiquitinated serotonin transporter obtained from the blood sample of the subject is more preferably 70% or less, even more preferably 50% or less, and yet even more preferably 40% or less with reference to the control. According to the selection of the above-described calculation formulae, "or more" may be more appropriate than "or less".

The method of the present invention preferably includes the addition of a proteasome inhibitor to the sample as described above, thereby improving the sensitivity for detection of the ubiquitinated serotonin transporter.

The time of treatment with the proteasome inhibitor is not particularly limited, but is preferably from 30 minutes to 48 hours, more preferably from 2 to 12 hours, and even more preferably 4 hours.

The temperature of treatment with the proteasome inhibitor is not particularly limited. For example, the temperature is preferably from 36 to 38° C., and more preferably 37° C.

The concentration of the proteasome inhibitor may be appropriately established according to the form of the sample. For example, the concentration is preferably from 1 to 200 µM, more preferably from 10 to 100 µM, and even more preferably 20 µM.

Based on the findings by the present inventors, degradation of the ubiquitinated serotonin transporter is closely related with depression. Accordingly, the proteasome inhibitor is useful as a depression test drug.

According to another embodiment of the method of the present invention, any sample other than the blood sample may be used as long as it can be obtained with maintaining the health of the subject and healthy subject. Examples of the other sample include cerebral fluid, lymph, neuron and tissues induced and differentiated from any cells or tissues using regenerative medical technique, and cells established from lymphocytes. In addition, a visualization technique may be used.

[Kit for Analyzing an Ubiquitinated Serotonin Transporter]

The kit of the present invention for analyzing an ubiquitinated serotonin transporter includes at least an ubiquitinated protein collector and an anti-serotonin transporter antibody. The order for using them is not limited, and the serotonin transporter and ubiquitinated serotonin transporter can be discriminated using them. In addition, they may be used in combination with other object. The kit of the present invention for analyzing an ubiquitinated serotonin transporter preferably further includes a proteasome inhibitor.

The kit for analyzing an ubiquitinated serotonin transporter is suitable for analyzing the amount of the ubiquitinated serotonin transporter contained in the sample. The analysis of the amount includes the measurement of the absolute amount in the sample and the measurement of the relative amount without limitation, and is a concept including the comparison with specific one or more other components. The kit is preferably suitable for the analysis of the above-described the proportion of the ubiquitinated serotonin transporter in the sample.

The sample in the kit of the present invention is not particularly limited as long as it contains an ubiquitinated serotonin transporter. Examples of the sample include, but not limited to, animals, plants, microorganisms, and objects obtained by the application of regenerative medical technology. The sample may be freely selected as appropriate from cells, tissues, organs, and individuals. The sample is preferably an sample obtained from an animal, more preferably an animal body fluid and a homogenate of an animal tissue or an organ, even more preferably a blood, yet even preferably a platelet fraction from the blood, and yet even preferably a leukocyte fraction containing lymphocytes, and particularly preferably a platelet fraction and a lymphocyte fraction. The sample may be appropriately obtained using a known common procedure.

The kit of the present invention is preferably used for diagnosing and determining depression. The kit is also suitable for carrying out the above-described method for utilizing a novel marker. In addition, the kit is also suitable for the diagnosis of other psychiatric disorders such as autism and Asperger's syndrome.

The ubiquitinated protein collector is not particularly limited as long as it can discriminate ubiquitin, and the discriminated protein can be collected. Examples of the collector include antibodies and beads for collecting protein combined with ubiquitin. The ubiquitinated protein collector may be a combination of one or more members, and may be selected as appropriate. Any commercial product may be appropriately used.

The anti-serotonin transporter antibody is not particularly limited, and may be a monoclonal antibody, a polyclonal antibody, or an artificially created antibody fragment. The anti-serotonin transporter antibody may be an appropriate commercial product.

The proteasome inhibitor is also not particularly limited, but is preferably MG-132 or lactacystin.

Examples of the autophagy inhibitor include 3-methyladenine, and examples of the protease inhibitor include E-64d.

The kit of the present invention may further contain an object suitable for the method for analyzing an ubiquitinated serotonin transporter. The analysis method is preferably the above-described quantification method. For example, the kit may contain various antibodies, enzymes, buffers, salts, culture media, culture materials such as a culture sheet, stabilizers, antiseptics, transformed cells, vectors for transformation, primers, probes, gene fragments, nucleic acids such as siRNA and shRNA, markers; appropriate labeling agents such as radioactive materials, fluorescent substances, and dyes; and containers such as reaction plates.

[Method for Utilizing a Novel Marker 2]

The second method for utilizing a novel marker according to the present invention uses the combination of the amounts of the serotonin transporters is used as the marker. Accordingly, the detection and measurement of the ubiquitinated serotonin transporter are not essential. The above-described terms are used basically in the same meaning in the following explanations. However, from the technical viewpoint, they are understood in the meanings suitable for the method of the present invention, and the terms are appropriately further explained as needed.

The method of the present invention includes a step of analyzing the amount of the untreated serotonin transporter and the amount of the inhibitor-treated serotonin transporter in a blood sample collected from a subject. Preferably the method is a method for diagnosing depression or a method for determining depression including the above step.

The method of the present invention does not necessarily include the detection and measurement of an ubiquitinated serotonin transporter. However, the blood sample may contain an ubiquitinated serotonin transporter. In the present method, "the amount of the serotonin transporter" preferably contains the amount of the ubiquitinated serotonin transporter. More specifically, it is preferred that "the amount of the serotonin transporter" be the whole amount of the serotonin transporter contained in the blood sample.

In order to analyze the amount of the untreated serotonin transporter and the amount of the inhibitor-treated serotonin transporter, at least two series of blood samples must be prepared. The method of the present invention uses not proportion but "amount", so that it is suitable for the comparative test when the samples are substantially in the same amount and of the same quality. Based on these viewpoints, the means for obtaining the blood sample from the subject or healthy subject is not limited. According to a preferred manner, firstly, all the blood samples are prepared at the same time, and then divided into two or more series for use. When the amount in the subject and the amount in the healthy subject are compared, the amounts of the blood samples in the subject and healthy subject are preferably equal.

Provided that the amounts of the samples used for the measurement are equal, the blood samples may be concentrated or diluted. In addition, the collection, handling, and fraction of the blood samples, purification and determination of the serotonin transporter may refer to the above-described explanations.

The amount of the untreated serotonin transporter means the amount of the serotonin transporter in the untreated blood sample.

The amount of the inhibitor-treated serotonin transporter means the amount of the serotonin transporter in the blood sample on which a proteasome inhibitor has been added. The proteasome inhibitor may refer to the above-described explanation. In the following explanation, the addition of the proteasome inhibitor on the blood sample may be referred to as inhibitor-treated.

As described above, the difference between the "untreated" and "inhibitor-treated" is the presence or absence of the addition of the proteasome inhibitor. The difference of the specific treatment between the "untreated" and "inhibitor-treated" is appropriately determined according to the measurement of the amount of the serotonin transporter. For example, "inhibitor-treated" means the addition of a proteasome inhibitor, and "untreated" may not involve any addition. In addition, for example, the treatment amount and concentration of the proteasome inhibitor, treatment time, and treatment temperature are appropriately adjusted with relation to, for example, the fraction, purification, and measurement. The method of the present invention utilizes the amount of the serotonin transporter, so that the analysis conditions other than the "untreated" and "inhibitor-treated" are preferably identical between the blood samples.

[Method for Making Comparison with a Healthy Subject]

In the second method for utilizing the novel marker according to the present invention, the method for making a comparison with the healthy subject is described below. The above-described seventh and eighth aspects of the present invention correspond to the method for making a comparison with the healthy subject.

The method of the present invention further includes a step of analyzing the amount of the untreated serotonin transporter and the amount of the inhibitor-treated serotonin transporter in the blood sample collected from the healthy subject. The healthy subject may refer to the above-described explanation. The method of the present invention can be carried out when there is a blood sample collected from at least one healthy subject. Alternatively, it is also preferred that blood samples collected from as much healthy subjects as possible be provided, and the amount of the untreated serotonin transporter and the amount of the inhibitor-treated serotonin transporter are analyzed individually, and the averages of the amounts are used in the method of the present invention.

The method of the present invention further includes any one or more comparison steps of the following (3) to (5), preferably includes any two comparison steps of the following (3) to (5), and more preferably includes all the comparison steps of (3) to (5). When the method includes any two comparison steps of (3) to (5), inclusion of the comparison step of (3) is preferred.

(3) The step of comparing the difference between the amount of the untreated serotonin transporter and the amount of the inhibitor-treated serotonin transporter obtained from the blood sample collected from the subject (hereinafter may be referred to as the difference between the untreated and inhibitor-treated amounts) and the difference between the untreated and inhibitor-treated amounts obtained from the blood sample collected from the healthy subject.

The difference between the untreated and inhibitor-treated amounts focuses the attention on the difference of the abundance of the serotonin transporter contained in the untreated and inhibitor-treated blood samples. What is important is to grasp the difference of the amounts of the serotonin transporter between the untreated and inhibitor-treated samples, and the symbol and the like in the operation may be selected as appropriate.

(4) The step of comparing the amount of the untreated serotonin transporter obtained from the blood sample collected from the subject with the amount of the untreated serotonin transporter obtained from the blood sample collected from the healthy subject.

When a healthy subject and a patient with depression are compared, the amount of the ubiquitinated serotonin transporter to be subjected to the subsequent degradation is likely smaller in the blood sample of the patient with depression. More specifically, the amount of the serotonin transporter is likely high in the patients with depression. Accordingly, it is also effective to focus the attention on the amount of the untreated serotonin transporter.

(5) The step of comparing the amount of the inhibitor-treated serotonin transporter obtained from the blood sample collected from the subject with the amount of the inhibitor-treated serotonin transporter obtained from the blood sample collected from the healthy subject.

The degradation of the ubiquitinated serotonin transporter is likely hindered by the addition of a proteasome inhibitor. More specifically, the amount of the serotonin transporter increases in a healthy subject, but such increase found in the healthy subject is not observed in a patient with depression. Accordingly, it is also effective to focus the attention on the amount of the inhibitor-treated serotonin transporter.

In addition, in the method of the present invention, it is preferred that the subject be determined to have depression when any one or more of the following (6) to (8) is applicable, more preferably any two or more of the (6) to (8) are applicable, and more preferably all of the (6) to (8) are applicable. It is considered that the more of the (6) to (8) is applicable, the higher the accuracy of the determination of depression. When any two of the (6) to (8) are applicable, it is preferred that the (6) be included in the two.

(6) In the case where the difference between the untreated and inhibitor-treated amounts obtained from the blood sample collected from the subject is smaller than the difference between the untreated and inhibitor-treated amounts obtained from the blood sample collected from the healthy subject.

When comparing a healthy subject and a patient with depression, the amount of the ubiquitinated serotonin transporter to be subjected to the subsequent degradation is likely smaller in the blood sample of the patient with depression. It is considered that the less the increase of the amount of the serotonin transporter by the addition of the proteasome inhibitor, the more excessive amount of serotonin transporter is present, and the higher the possibility of having depression. Accordingly, it is considered that the smaller the difference of the amounts of the serotonin transporter between the untreated and inhibitor-treated samples, the higher the possibility of having depression.

The statement that "the amount difference is small" means that the difference of the abundance of the serotonin transporter between the untreated and inhibitor-treated blood samples is small. Accordingly, for some operation methods, the judgment as "the amount difference is small" may be appropriate even if the obtained value is high.

For example, when the amount difference is operated with the proportion (%) of the amount of the inhibitor-treated serotonin transporter to the amount of the untreated serotonin transporter as the control, the judgment as "the amount difference is small" is made preferably when the proportion in the subject is smaller than the proportion in the healthy subject, more preferably the proportion in the subject is smaller than the proportion in the healthy subject by 10%, even more preferably by 15%, and particularly preferably by 20%.

(7) In the case where the amount of the untreated serotonin transporter obtained from the blood sample collected from the subject is larger than the amount of the untreated serotonin transporter obtained from the blood sample collected from the healthy subject.

When comparing the healthy subject with the patient with depression, the amount of the ubiquitinated serotonin transporter to be subjected to the subsequent degradation is likely smaller in the blood sample of a patient with depression. More specifically, in an untreated state, it is considered that the amount of the serotonin transporter in the blood sample is larger in the patient with depression than in the healthy subject.

The "larger" means that the abundance of the serotonin transporter is larger in the blood sample of the subject than in the blood sample of the healthy subject as a result of the comparison of the abundance of the serotonin transporter contained in the untreated blood samples of the subject and healthy subject. Accordingly, for some operation methods, the judgment as "larger" may be appropriate even if the obtained value is small.

For example, when the amount of the untreated serotonin transporter obtained from the subject is operated with the proportion to the amount of the untreated serotonin transporter obtained from the healthy subject as the control, it is preferred that the judgment as "larger" be made when the amount of the untreated serotonin transporter obtained from the subject exceeds the control (set as 100%). It is more preferred that the judgment as "larger" be made when the amount of the untreated serotonin transporter obtained from the subject is 110% or more, even more preferably 135% or more, and particularly preferably 150% or more.

(8) In the case where the amount of the inhibitor-treated serotonin transporter obtained from the blood sample collected from the subject is smaller than the amount of the inhibitor-treated serotonin transporter obtained from the blood sample collected from the healthy subject.

It is considered that the progress of the degradation of the ubiquitinated serotonin transporter is hindered by the addition of the proteasome inhibitor. More specifically, the amount of the serotonin transporter increases in a healthy subject, but such increase in the healthy subject is not observed in a patient with depression. In the below-described example, the whole amount of the inhibitor-treated serotonin transporter obtained from the blood sample of the healthy subject was larger than the amount in the patient with depression.

The statement that "smaller" means the result that the abundance of the serotonin transporter contained in the inhibitor-treated blood sample of the subject is smaller than that in the healthy subject. Accordingly, for some operation methods, the judgment as "smaller" may be appropriate even if the obtained value is high.

For example, when the amount of the inhibitor-treated serotonin transporter obtained from the subject is operated with the proportion to the amount of the inhibitor-treated serotonin transporter obtained from the healthy subject as the control, it is preferred that the judgment as "smaller" be made when the amount of the inhibitor-treated serotonin transporter obtained from the subject is less than the control (set as 100%), more preferably the amount of the inhibitor-treated serotonin transporter obtained from the subject is 90% or less, more preferably 85% or less, and particularly preferably 80% or less.

[Method for Using the Blood Sample of the Subject Alone]

In the second method according to the present invention for utilizing the novel marker, the method for using the blood sample of the subject alone is described below. The above-described ninth aspect of the present invention corresponds to the method using the blood sample of the subject alone. The above-described terms used in "Method for making comparison with a healthy subject" are used basically in the same meaning in the following explanation.

The method of the present invention uses the amounts of the inhibitor-treated and untreated serotonin transporters obtained from the blood sample collected from the subject. The method is simple because it does not require the blood sample of a healthy subject.

The method of the present invention determines that the subject has depression when the amount of the inhibitor-treated serotonin transporter obtained from the blood sample collected from the subject is 1.7 times or less, preferably 1.3 times or less, and more preferably 1.1 times or less the amount of the untreated serotonin transporter. In the method of the present invention, it is important to grasp the difference of the serotonin transporter abundance between the untreated and inhibitor-treated blood samples in a certain size. Accordingly, when the operation method is different, "1.7 times or less" may be applicable even if the value is different.

When the operation method for the comparison is changed, the criteria such as "1.7 times or less" may change. Accordingly, the method of the present invention is a method for diagnosing or determining depression from the amounts of the untreated and inhibitor-treated serotonin transporters, and includes the embodiments which conform to the above operation of the method of the present invention.

Based on the findings by the present inventor, it is considered that the less the increase of the serotonin transporter by the addition of the proteasome inhibitor, or the lower the proportion of the ubiquitinated serotonin transporter, the higher the possibility of having depression. Accordingly, it is considered that the closer the amount of the inhibitor-treated serotonin transporter obtained from the blood sample collected from the subject to the amount of the untreated serotonin transporter, the higher the possibility of having depression.

The second method according to the present invention for utilizing a novel marker may follow other embodiment. The explanation of the above-described other embodiment in "Method for utilizing a novel marker" may be referred to.

The above-described method for utilizing a novel marker, and the second method for utilizing a novel marker may be used as a support for the diagnosis of depression.

[Kit for Analyzing a Serotonin Transporter]

The kit for analyzing a serotonin transporter includes at least a proteasome inhibitor and an anti-serotonin transporter antibody. The kit may be used in combination with other object.

The order of use is not particularly limited. It is preferred that the amounts of the above-described untreated and inhibitor-treated serotonin transporters be measured using the kit.

The kit for analyzing a serotonin transporter is suitable for analyzing the amount of the serotonin transporter contained in the sample, and also suitable for measuring the absolute amount of the serotonin transporter contained in the sample.

The sample in the kit of the present invention is not particularly limited as long as it contains a serotonin transporter. The sample may contain an ubiquitinated serotonin transporter. Examples of the sample include, but not limited to, animals, plants, microorganisms, and objects obtained by the application of regenerative medical technology. The sample may be freely selected as appropriate from cells, tissues, organs, and individuals. The sample is preferably an sample obtained from an animal, more preferably an animal body fluid and a homogenate of an animal tissue or an organ, even more preferably a blood, yet even preferably a platelet fraction from the blood, and yet even preferably a leukocyte fraction containing lymphocytes, and particularly preferably a platelet fraction and a lymphocyte fraction. The sample may be appropriately obtained using a known common procedure.

The use of the kit of the present invention, the anti-serotonin transporter antibody, proteasome inhibitor, and additional objects contained in the kit of the present invention may refer to the explanation of the "Kit for analyzing a ubiquitinated serotonin transporter".

EXAMPLES

Examples of the present invention are described below. The technical scope of the present invention will not be limited to the following examples.

(A) Method and Material

[(1) Making of MAGE-D1 (Melanoma Antigen Gene-D1) Gene-Deficient Mouse]

The targeting vector (Stratagene: pBlueScript), which allow homologous recombination between the MAGE-D1 gene (Gene bank: NM_019791.2) exon and the drug (G418)-resistant gene (GenBank: U00004.1), was electroporated into the embryonic stem (ES) cells (acquired from Research Institute of National Center for Geriatrics and Gerontology) derived from the 129Svj mouse, and the drug-resistant colony was selected. The homologous recombinant was identified from the selected resistant colony by Southern blotting. The desired homologous recombinant ES cell clone thus identified was injected into the blastocyst stage embryo of the C57BL/6J mouse, thereby making a chimera mouse. The chimera mouse was mated with the wild type C57BL/6J mouse, thereby making a hetero MAGE-D1 gene-deficient mouse of F1 generation. The wild type C57BL/6J was mated with the hetero MAGE-D1 gene-deficient mouse up to the F10 generation, and the mouse having 99.9 percent (as a result of one mating with the C57BL/6J mouse, about half the genes of the newborn mouse are derived from the C57BL/6J mouse used for mating; in other words, as a result of the n times of mating with the C57BL/6J mouse, about $[1-(½)^{n+1}] \times 100\%$ genes are likely derived from the C57BL/6J mouse) C57BL/6J genetic background was used. The mouse having the genetic background was used as the MAGE-D1 gene-deficient mouse (hereinafter may be referred to as model mouse) in the following test.

[(2) Making of Recombinant MAGE-D1 Vector and Cell Line Constitutively Expressing Serotonin Transporter]

The full length of the MAGE-D1 gene (Gene bank: NM_019791.2) cloned from the mouse cDNA library was bound with the tag gene (the sequence of the gene is set forth in SEQ ID NO. 1) of the hemagglutinin (HA) sequence of the influenza A virus (the sequence is set forth in SEQ ID NO. 8), and inserted into the pcDNA3 vector (Invitrogen, Carlsbad, Calif.).

SEQ ID NO. 1: 5'-TACCCCTACGACGTGCCCGACTACGCC-3'

SEQ ID NO. 8: tyrosine-proline-tyrosine-aspartic acid-valine-proline-aspartic acid-tyrosine-alanine The serotonin transporter (hereinafter may be referred to as SERT) gene (rat: Gene bank: NM_013034.3; for reference, mouse: the same data base: NM_010484.2) cloned from the rat cDNA library was inserted into the pcDNA3 vector.

The pcDNA3 vector into which the above-described serotonin transporter gene had been inserted was genetically introduced into Chinese hamster ovary cells using FuGENE 6 (Rosche), thereby making the cell line constitutively expressing the serotonin transporter gene.

In addition, the MAGE-D1 gene introduction into the cell line constitutively expressing the serotonin transporter gene was carried out by the above-described MAGE-D1 gene and the pcDNA3 vector into which the HA-tagged gene had been inserted, using FuGENE 6 (Roche Diagnostics, Mannheim, Germany).

[(3) Evaluation of Depression-Like Behavior by Forced Swimming Test]

Experimental equipment and procedure: the experimental equipment was a water tank (diameter 15 cm×height 20 cm) containing water (water temperature about 22° C.×depth 13 cm). The wild type C57BL/6J mouse as the control or the model mouse was placed in the water tank, and immediately after that, the immobility time was measured using Scanet MV-10AQ (Brainscience Idea, Co., Ltd. Osaka, Japan) for 10 minutes at intervals of 1 minute.

5 or 10 mg/kg sertraline (Pfizer, Groton, Conn.) suspended in 0.3% carboxymethyl cellulose sodium, and 10 or 20 mg/kg imipramine (Sigma, St. Louis, Mo.) dissolved in a normal saline solution were intraperitoneally administered 30 minutes before the main test. As the control, the solvent was intraperitoneally administered.

[(4) Evaluation of Serotonin Releasing Capacity by In Vivo Microdialysis]

A mouse under anesthesia with pentobarbital sodium (50 mg/kg, i.p.) was fixed on a brain fixer, a guide cannula (AG-6, EICOM Corp., Kyoto, Japan) was inserted into the frontal cortex (from the cruciate-suture on the skull to the rostral end: 1.7 mm right side: +1.0 mm depth: −1.5 mm) at a 15° angle, referring to the brain map (Franklin and Paxinos, 1997). The guide cannula was fixed on the skull using dental cement (SHOFU Inc., Kyoto, Japan).

On the day following the surgery, Dialysis Probe (A-I-6-1, 1 mm membrane length, EICOM Corp.) was inserted into the frontal cortex of the mouse from the guide cannula and the mouse was placed in an acryl case (30 cm×30 cm×35 cm), and allowed to freely move. A Ringer's solution (NaCl: 147 mM, KCl: 4 mM, $CaCl_2$: 2.3 mM) was perfused in the probe at a flow rate of 1.0 µl/min. The perfusate was collected at intervals of 10 minutes, and the serotonin content in the collected liquid was quantitated by high performance liquid chromatography (HTEC-500, EICOM Corp.). The mobile phase was a 99% (v/v) 0.1M sodium phosphate buffer (pH 6.0) containing 1% (v/v) methanol, sodium decanesulfonate (SDS, 500 mg/L), and EDTA-2Na (50 mg/L), and flown at a flow rate of 500 µl/min. The analysis was carried out using a separation column (EICOMPAK PP-ODS, 30×4.6 mm phi, EICOM Corp.) and a precolumn (EICOM PREPAKSET CA-ODS, EICOM Corp.), an electrochemical detector equipped with a graphite electrode (WE-3G) as the working electrode was used for detection, and the preset potential was +400 mV vs. Ag/AgCl.

The time schedule was as follows: after the amount of the extracellular free serotonin became stable (−60 to 0 minute), a high potassium Ringer's solution (NaCl: 101 mM, KCl: 50 mM, $CaCl_2$: 2.3 mM) was perfused in the probe for 20 minutes (0 to 20 minutes), and then the perfusate was returned to the Ringer's solution, and the amount of the extracellular free serotonin was measured up to 1 hour.

[(5) Evaluation of the Expression Amount of Serotonin Transporter Protein by Western Blotting]

The mouse brain sample, cells, and established lymphocytes were subjected to ultrasonic fragmentation at 4° C. using a sonicator in a lysis buffer [20 mM Tris-HCl, 150 mM NaCl, 50 mM NaF, 1 mM EDTA, 1 mM EGTA, 1% (w/v) TRITONX-100, 1 mM sodium orthovanadate, 0.1% (w/v) SDS, 1% (w/v) sodium deoxycholate, 0.5 mM dithiothreitol; 10 mM sodium pyrophosphate decahydrate, 1 mM phenylmethylsulfonyl fluoride, 10 µg/mL aprotinin, 10 µg/mL leupeptin, and 10 µg/mL pepstatin (pH 7.4)], and thus a homogenate was obtained through these operations. The homogenate was centrifuged for 20 minutes at 4° C. and 13000×g, and the supernatant thus obtained was used. A sample buffer [0.125 M Tris-HCl (pH 6.8), 2% (w/v) SDS, 5% (w/v) glycerol, 0.002% (w/v) bromphenol blue, and 5% (w/v) 2-mercaptoethanol] was added to each of the supernatant samples whose protein content had been adjusted, and then boiled at 95° C. for 5 minutes. Thereafter, the protein (20 g) was subjected to electrophoresis using a 10% polyacrylamide gel, the protein was transferred to a polyvinylidene difluoride (PVDF) membrane (Millipore Corporation, Billerica, Mass., USA), and blocked using Detector Block Kit (Kirkegaard and Perry Laboratories, Gaithersburg, Md., USA). A primary antibody (anti-SERT) (Millipore, Billerica, Mass.) against the serotonin transporter protein was added to the PVDF membrane, allowed to stand overnight in a refrigerator (4° C.), and then a secondary antibody (HRP-conjugated anti-rabbit IgG) (Kirkegaard and Perry Laboratories) was added, and allowed to stand at room temperature for 3 hours. The luminescence due to the immune complex was detected using ECL (GE Healthcare Biosciences, Piscataway, N.J., USA), which is a Western blotting detection reagent, and the expression amount was calculated by the image analysis of the luminescence intensity.

Subsequently, in order to determine the expression amount of the β-actin protein as the endogenous reference material, stripping was carried out, a primary antibody (anti-β-actin) (Santa Cruz Biotechnology, Santa Cruz, Calif.) was added, and incubated. In the result thus obtained, the band of the serotonin transporter protein was corrected by the band of the β actin protein, and the expression amount to the control group was expressed in terms of the percentage (%).

[(6) Evaluation of the Expression Amount of Ubiquitinated Serotonin Transporter Protein]

According to the procedure in the above-described A (5), the ubiquitinated protein was isolated from the homogenate homogenized with a lysis buffer using UBIQAPTURE-Q kit (Enzo Life Sciences International, Inc, Plymouth Meeting, Pa.), and the ubiquitinated serotonin transporter protein was detected by Western blotting under the same conditions as in the A (5).

[(7) Evaluation of Binding Between MAGE-D1 Protein and Serotonin Transporter Protein by Immunoprecipitation]

The homogenate of the brain or culture cells prepared under the same conditions as in the A (5) was mixed with the anti-HA-tag (Medical & Biological Laboratories, Nagoya, Japan), which is an antibody to the HA-tagged protein, or the anti-SERT, which is an antibody to the serotonin transporter protein, and DYNABEADS protein A (Invitrogen), and the mixture was incubated under rotation, thereby forming a DYNABEADS-antigen-antibody complex composed of the DYNABEADS, antibody, and the antigen which is detected by the antibody in the sample (HA-tagged MAGE-D1 protein or serotonin transporter protein). The DYNABEADS-antigen-antibody complex was heated in the sample buffer under the same conditions as in the A (5), and the complex was eluted from the DYNABEADS. The elution sample was subjected to Western blotting using the antibody anti-SERT or antibody anti-MAGE-D1 (Millipore) under the same conditions as in the A (5).

[(8) Quantitative Evaluation of Serotonin Transporter mRNA]

The total RNA was extracted from the frontal cortex of the wild type C57BL/6J mouse as the control and the model mouse, and the cDNA synthesized by a reverse transcriptase was used as the template for the real time RT-PCR. The amount of the mRNA expression was quantitated by the Taqman probe method. For the SERT gene, the primers set forth in SEQ ID NOs. 2 and 3, and the Taqman probe set forth in SEQ ID NO. 4 were used.

SEQ ID NO. 2: 5'-GGATTTCCTCCTGTCTGTCATTGG-3'

SEQ ID NO. 3: 5'-CCACCATTCTGGTAGCATATGTAGG-3'

SEQ ID NO. 4: 5'-CCGTGGACCTGGGCAACATCTGGC-3'

For the β actin used as the internal standard, the primers set forth in SEQ ID NOs. 5 and 6, and the Taqman probe set forth in SEQ ID NO. 7 were used.

```
SEQ ID NO. 5: 5'-GGGCTATGCTCTCCCTCACG-3'

SEQ ID NO. 6: 5'-GTCACGCACGATTTCCCTCTC-3'

SEQ ID NO. 7: 5'-CCTGCGTCTGGACCTGGCTGGC-3'
```

If the sequence described herein does not agree with that in the sequence list, the sequence described herein takes precedence.

[(9) Evaluation of Serotonin Transporter Function by the Measurement of Serotonin Reuptake Activity]

The cell line constitutively expressing the serotonin transporter gene was seeded on a 24-well plate, and the MAGE-D1 gene was introduced thereto. 48 hours after the gene introduction, the radiolabeled [$^3$H] serotonin was added to the cells in the Krebs-Ringer HEPES buffer [130 mM NaCl, 1.3 mM KCl, 2.2 mM CaCl$_2$, 1.2 mM MgSO$_4$, 1.2 mM KH$_2$PO$_4$, 1.8 g/L glucose, and 10 mM HEPES (pH 7.4)] to make the final concentration 20 nM, and incubated at 37° C. for 10 minutes. The excessive portion of the [$^3$H] serotonin in the buffer was removed, and the cells were dissolved in 1 N NaOH. The [$^3$H] serotonin taken into the cells were counted by a liquid scintillation counter, thereby evaluating the uptake activity. Unlabeled serotonin at different concentrations was added together with the [$^3$H] serotonin, and the binding affinity (Km) and the maximum binding amount (Vmax) were determined by the kinetic analysis.

[(10) Making of Established Lymphocytes from the Blood of Healthy Subjects and Patients with Depression]

The objects were healthy subjects, patients with depression effectively treated with the antidepressant fluvoxamine, which is a selective serotonin reuptake inhibitor, and the patients with depression resistant to the drug. The patients with depression were those diagnosed to have depression by a physician based on the Hamilton Depression Scale (HAM-D). The healthy subjects were those identified as healthy subjects by a physician.

Each of the blood samples aseptically collected from the above objects was diluted two folds with a sterile normal saline solution. Subsequently, the diluted blood sample was quietly poured into the tube containing 3.5 ml of the Ficoll-Paque liquid (General Electric Company, Uppsala, Sweden), and centrifuged at 600×g for 30 minutes. Subsequently, the white layer of mononuclear cells at the intermediate part of the centrifuged sample, and the Ficoll-Paque liquid layer immediately below the mononuclear cell layer were collected. Subsequently, the collected sample was suspended in a normal saline solution, and centrifuged at 400×g for 30 minutes. Subsequently, a normal saline solution was added to the precipitate obtained by the centrifugation, and centrifuged at 240×g for 5 minutes. Subsequently, the liquid medium (RPMI1640) was added to the precipitate obtained by the centrifugation, and centrifuged again at 240×g for 5 minutes. Subsequently, the precipitate obtained by the centrifugation was used as the lymphocyte fraction, and cultured in RPMI1640 containing 20% fetus bovine blood serum, 20% the culture supernatant of Epstein-Barr virus-releasing cell line (B95-8), and 2 μg/ml cyclosporine A. The mixture was cultured for one week or more, and those showed proliferation were used as the established lymphocytes, and subcultivated in RPMI1640 containing 10% fetus bovine blood serum. The evaluation of the expression amount of the serotonin transporter protein contained in the established lymphocytes prepared from the blood of the object, and the evaluation of the expression amount of the ubiquitinated serotonin transporter protein were carried out in the same manner as in the above-described A (5) and A (6).

(B) Result

[MAGE-D1 Gene-Deficient Mouse]

In the present example, the model animal was the MAGE-D1 gene-deficient mouse. As the evaluation of the depression-like behavior, the forced swimming test was used. The mouse placed in a narrow cylinder filled with water recognized that it cannot escape there from, and the time that the mouse floats on water without moving is evaluated as the decrease of motivation. The model mouse showed the increase of the immobility time, which indicates the decrease in motivation, in the forced swimming test, and both of the sertraline, which is a selective serotonin reuptake inhibitor, and imipramine, which is a tricyclic antidepressant, significantly and dose-dependently decreased the increase of the immobility time (FIG. 1). Each study was carried out three times, and FIG. 1 was prepared based on the average. The average of the immobility time ratio was as follows: in the sertraline administration test, for the control mouse, 45.7% at 0 mg/kg, 37.4% at 5 mg/kg, and 37.7% at 10 mg/kg; for the model mouse, 64.5% at 0 mg/kg, 56.3% at 5 mg/kg, and 45.7% at 10 mg/kg. In the imipramine administration test, for the control mouse, 41.7% at 0 mg/kg, 47.7% at 10 mg/kg, and 39.0% at 20 mg/kg; for the model mouse, 67.0% at 0 mg/kg, 60.2% at 10 mg/kg, and 40.6% at 20 mg/kg.

It was suggested that the model mouse shows the depression-like behavior highly responsive to a human antidepressant. The depression-like behavior of the model mouse is remitted by a human antidepressant, so that it is rationally presumed that the effect observed in the model mouse is also effective in human. It is also rationally presumed that the depression mechanism in the model mouse is common with that in human.

One of the clinical conditions of depression is a monoamine hypothesis, and in particular the serotonergic nervous system has been attracting attention as the target of antidepressants. The function of the serotoninergic nervous system in the model mouse was evaluated using the microdialysis method. In the frontal cortex in the model mouse, the increase in the amount of the extracellular serotonin caused by high potassium stimulation was significantly reduced in comparison with that in the control mouse (FIG. 2).

Figure 2:
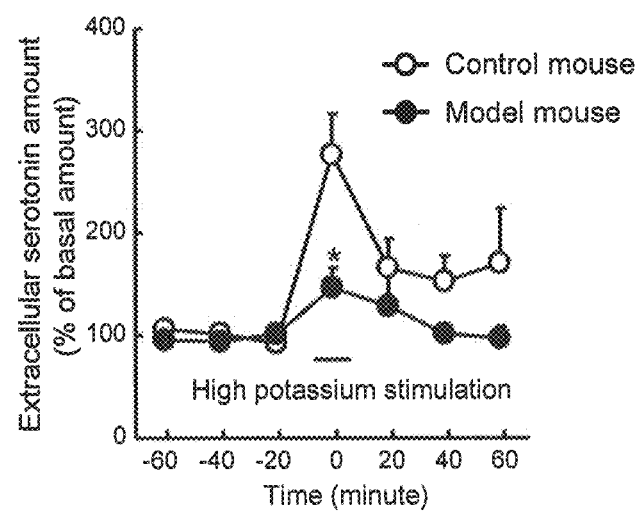
FIG. 2 shows that the increase of the amount of the released extracellular serotonin by stimulation with high potassium is significantly decreased in the model mouse.

The model and control mice were each subjected to five times of tests, and FIG. 2 was made based on the average. The basal extracellular amount is the average of the serotonin concentration in the dialysate, which was flown from the mouse brain at a rate of 1 μl/min, collected for 10 minutes three times from −60 to −20 minutes, and 0.46±0.21 pmol/10 μl/10 min for the model mouse, 0.55±0.13 pmol/10 μl/10 min for the control mouse. FIG. 2 shows the proportion with reference to the basal extracellular amount.

The average of the extracellular serotonin amount in the control mice was as follows: 275.9% after 0 minute (immediately after the application of high potassium stimulation), 165.2% after 20 minutes, 152.0% after 40 minutes, and 169.9% after 60 minutes; in the model mice, 146.5% after 0 minute, 128.1% after 20 minutes, 101.2% after 40 minutes, and 97.5% after 60 minutes. The decline in function of the serotoninergic nervous system in the model mice was suggested.

[MAGE-D1 Gene Overexpression System]

Figure 3:
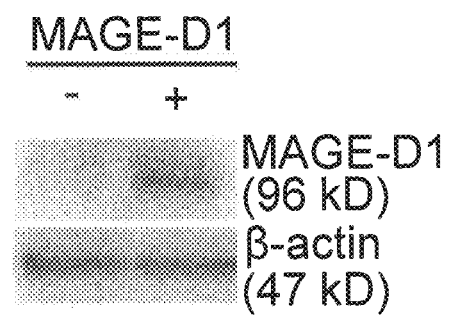
FIG. 3 shows that the MAGE-D1 gene overexpression system is adequate for the examination of the influence of the overexpression of the MAGE-D1 gene.

According to the procedure described in the above A (2), the HA-tagged MAGE-D1 gene was forcedly expressed in the cell line constitutively expressing the serotonin transporter gene by transfection, and the cell line was used as the MAGE-D1 gene overexpression system. As the control, the pcDNA3 vector which forcedly expresses the HA-tagged gene alone (not having the MAGE-D1 gene) was subjected to transfection. According to Western blotting using the anti-MAGE-D1 antibody (under the same conditions as in A (5)), overexpression of the MAGE-D1 protein (96 kD) was found in the MAGE-D1 gene overexpression system, and it was confirmed that the system is suitable for the examination of the influence of the MAGE-D1 gene overexpression (FIG. 3). There was no marked influence of the MAGE-D1 gene overexpression on the cell survival.

Example 1

Expression of Serotonin Transporter in MAGE-D1 Gene-Deficient Mouse

Figure 4:
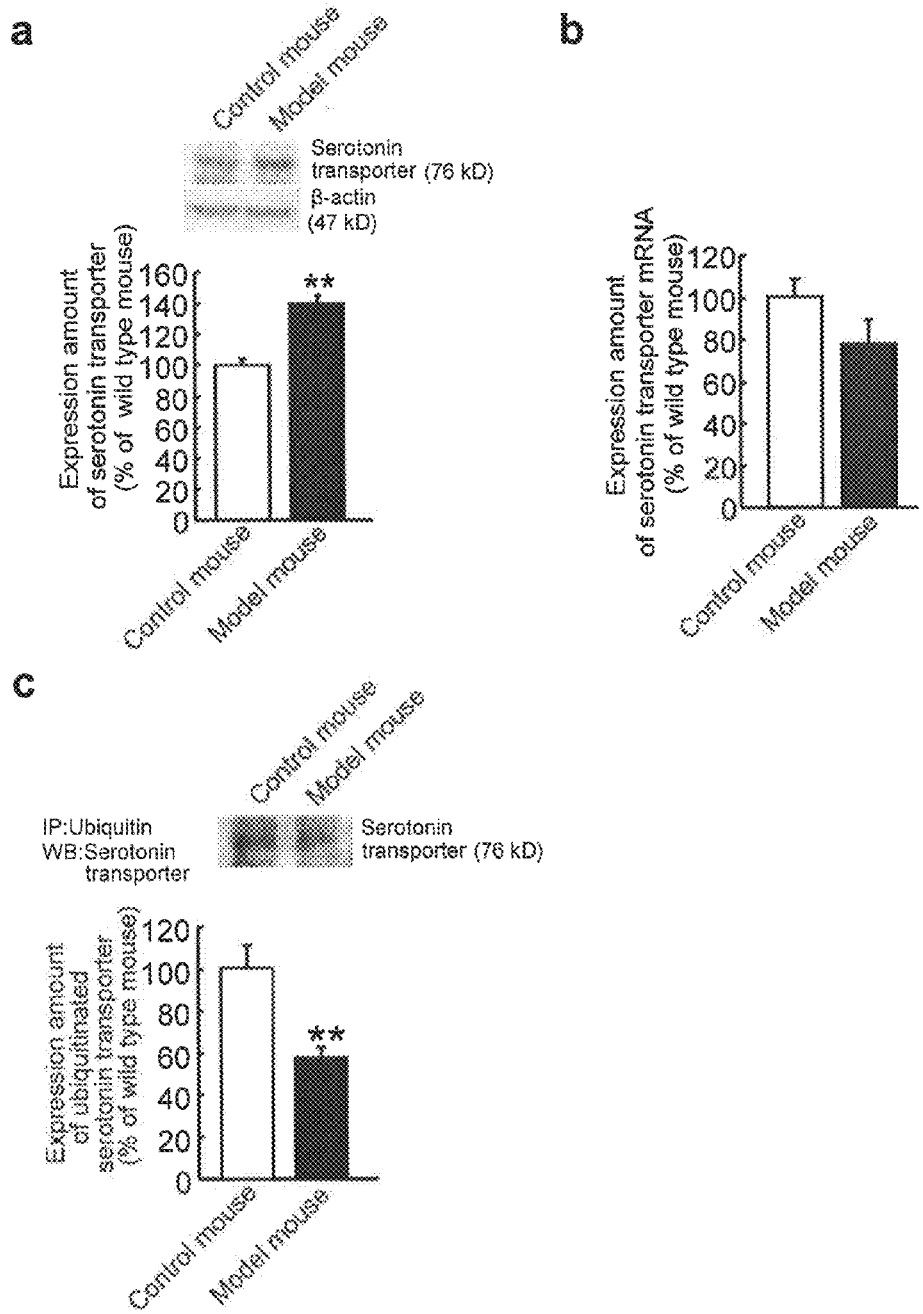
FIG. 4(a) shows that the amount of the serotonin transporter protein increased in the frontal cortex of the model mouse.
FIG. 4(b) shows that there was no significant difference in the amount of the serotonin transporter mRNA between the model and control mice.
FIG. 4(c) shows that the amount of the ubiquitinated serotonin transporter protein significantly decreased in the model mouse.

Using the model mouse and the wild type C57BL/6J as the control, in order to find the cause of the decline in function of the serotoninergic nervous system in the model mouse, the change in the expression of the serotonin transporter protein in the frontal cortex was studied by Western blotting described in the A (5) and immunostaining described in the A (7); the increase in the amount of the serotonin transporter protein (76 kD) was found in the frontal cortex of the model mouse (FIG. 4a: 127.4% with reference to control mouse). In order to study the participation of transcriptional control in the increase in the amount of the serotonin transporter protein, the serotonin transporter mRNA was quantitated by the real time PCR method described in the A (8). There was no difference in the amount of the serotonin transporter mRNA between the model and control mice (FIG. 4b: 77.5% with reference to the control mouse). On the other hand, ubiquitination in the participation of protein degradation of the serotonin transporter protein was studied by the procedure described in the A (6), and the significant decrease in the ubiquitinated serotonin transporter protein in the model mouse was observed (FIG. 4c: 57.6% with reference to the control mouse). It was suggested that the deficiency of the MAGE-D1 gene decreases the metabolism of the serotonin transporter protein through ubiquitination, and increases the amount of the serotonin transporter protein in the model mouse.

The tests the results of which are shown in FIGS. 4a to 4c were carried out three times for the model and control mice, and the results are recorded as averages.

Example 2

Interaction Between MAGE-D1 Protein and Serotonin Transporter Protein

Figure 5:
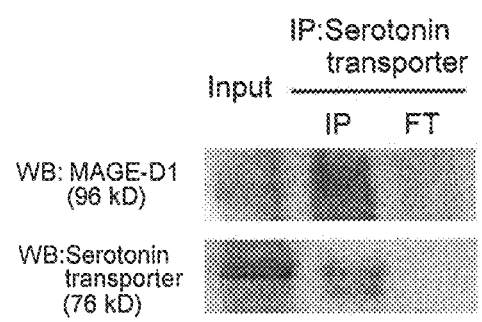
FIG. 5 shows the data suggesting that the serotonin transporter protein binds with the MAGE-D1 protein.

As the interaction between the MAGE-D1 protein and serotonin transporter protein, the binding between them was analyzed by the immunoprecipitation method. The homogenate of the model mouse brain was prepared according to the procedure described in the A (5), and subjected to immunoprecipitation using the DYNABEADS protein A and the anti-SERT antibody. The MAGE-D1 protein coprecipitated with the serotonin transporter protein was detected by Western blotting using the anti-MAGE-D1 antibody (center lane in FIG. 5).

Figure 6:
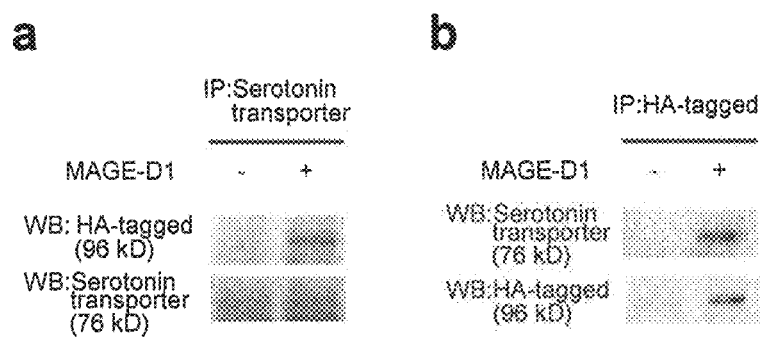
FIGS. 6(a) and 6(b) show the data suggesting that the serotonin transporter protein binds with the MAGE-D1 protein.

The homogenate of the cell line constitutively expressing the serotonin transporter gene to which the HA-tagged MAGE-D1 gene had been introduced was prepared in the same manner as for the homogenate of the model mouse brain, and subjected to immunoprecipitation using the DYNABEADS protein A and the anti-SERT antibody or anti-HA antibody. The MAGE-D1 protein coprecipitated with the serotonin transporter protein was detected by Western blotting using the anti-HA antibody under the same conditions as in the A (5) (FIG. 6a). In the same manner, the serotonin transporter protein coprecipitated with the MAGE-D1 protein was detected by Western blotting under the same conditions as the A (5) which used the anti-SERT antibody (FIG. 6b).

It was suggested that the MAGE-D1 protein was bound and interacted with the serotonin transporter protein.

Example 3

Interaction Between the MAGE-D1 Protein and Serotonin Transporter Protein 2

Figure 7:
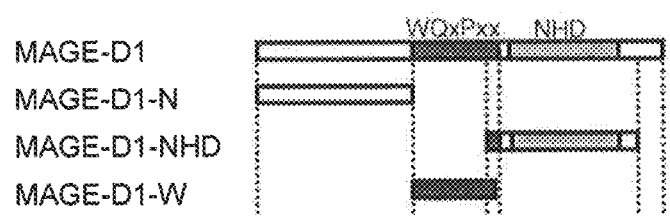
FIG. 7 (a) shows the schematic diagram of the MAGE-D1 gene, and the schematic diagrams of the MAGE-D1 partially constructed genes used in Examples.
Figure 7:
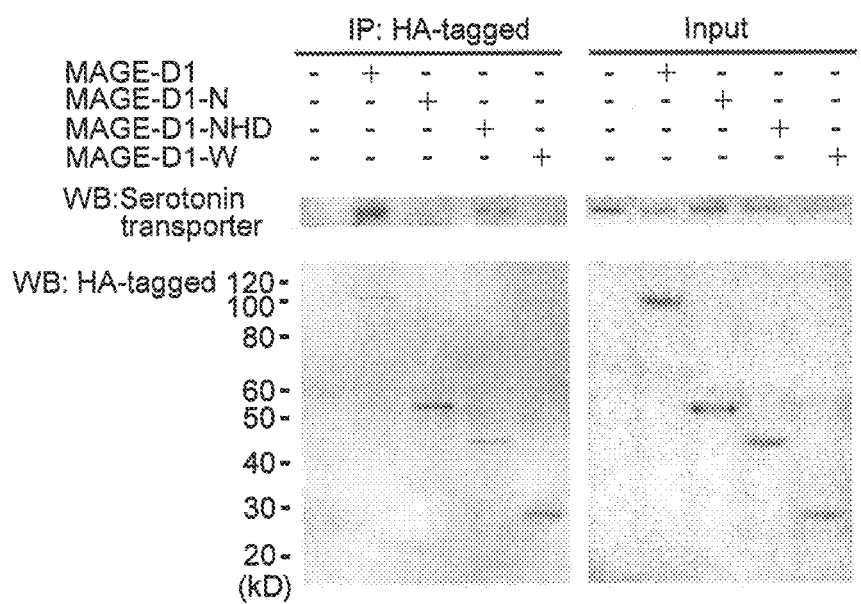

The MAGE-D1 protein includes a specific N-terminal domain, a tryptophan-glutamine-x-proline-x-x (WQxPxx) repetition domain, and a necdin homology (NHD) domain at the C-terminal side (FIG. 7a "MAGE-D1" shows a schematic diagram). Therefore, the domain of the MAGE-D1 protein important for the binding with the serotonin transporter protein was specified. In the same manner as in the A (2), the homogenates of the cell line constitutively expressing the serotonin transporter gene to which any of the vectors expressing the partially constructed HA-tagged MAGE-D1 genes (MAGE-D1-N, MAGE-D1-NHD, and MAGE-D1-W; the schematic diagrams of these partially constructed genes are shown in FIG. 7a) had been transfected were prepared in the same manner as in the A (5), and subjected to immunoprecipitation using the DYNABEADS protein A and anti-HA antibody. The serotonin transporter protein coprecipitated with the MAGE-D1-NHD protein was detected by Western blotting (FIG. 7b) using the anti-SERT antibody. It was suggested that the MAGE-D1 protein is bound to and interacted with the serotonin transporter protein through the NHD domain.

Example 4

Influence of Forced Expression of MAGE-D1 Gene on Serotonin Transporter Protein

According to the procedure described in the A (2), the MAGE-D1 gene was forcedly expressed in the cell line constitutively expressing the serotonin transporter gene by gene introduction, and the influence on the expression amount of the serotonin transporter protein by the MAGE-D1 protein and the serotonin reuptake activity was studied. The control (MAGE-D1-) was the cell line constitutively expressing the serotonin transporter gene.

Figure 8:
FIG. 8(a) shows that the expression of the serotonin transporter protein decreased by the forced expression of the MAGE-D1 protein.
FIG. 8(b) shows that the serotonin reuptake activity decreased by the forced expression of the MAGE-D1 protein.
Figure 8:
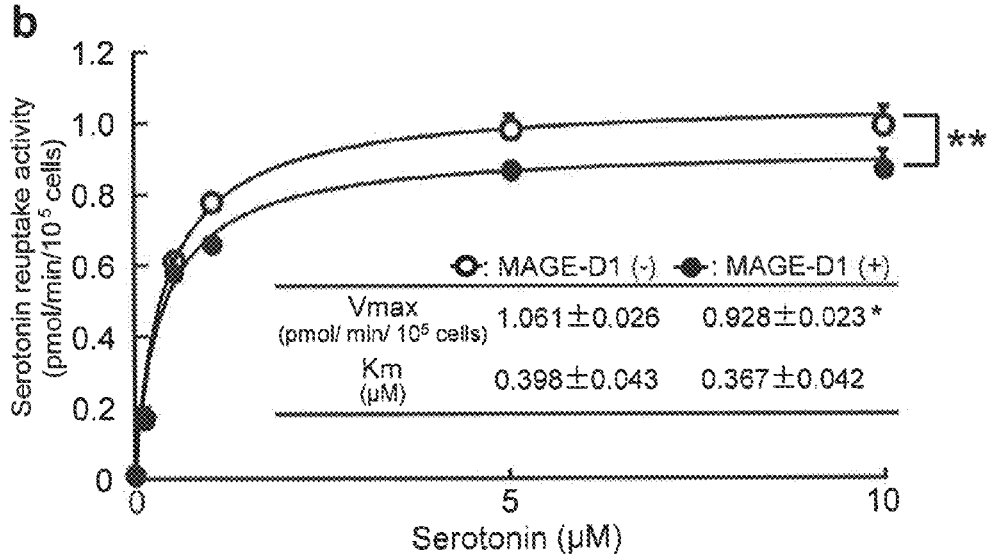

In the cell line constitutively expressing the serotonin transporter gene 48 hours after the introduction of the MAGE-D1 gene, the decrease in the expression of the serotonin transporter protein caused by the forced expression of the MAGE-D1 protein was found by Western blotting under the same conditions as in the A (5) using the anti-SERT antibody (FIG. 8a, 85.1% with reference to the control), and the decrease in the V max value was found by the kinetic analysis in the measurement of the serotonin reuptake activity (FIG. 8b).

Each study was carried out three times, and the results are recorded as averages.

Example 5

Participation of Ubiquitination by MAGE-D1 Protein in Degradation of Serotonin Transporter In order to study the participation of proteasome in the metabolism of the SERT protein, the influence of the proteasome inhibitor (MG132) on the cell line constitutively expressing the SERT gene was studied.

Figure 9:
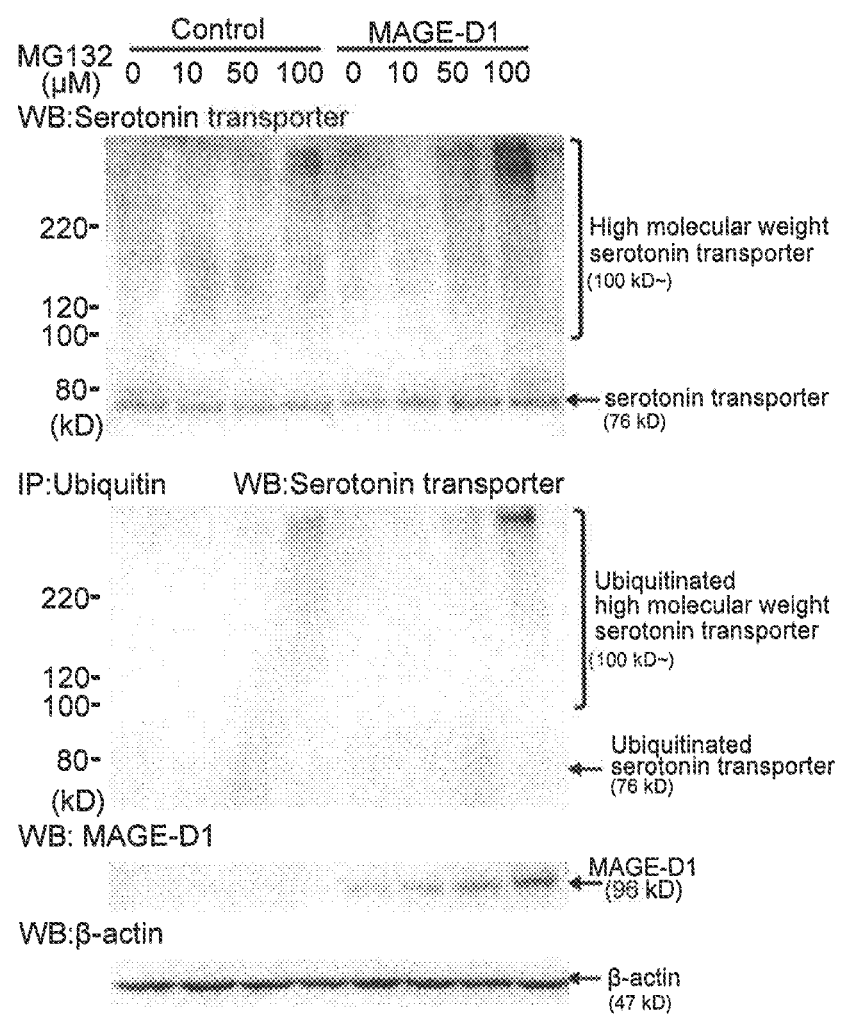
FIG. 9 shows that the serotonin transporter protein gained molecular weight by ubiquitination, and that the amount of the ubiquitinated serotonin transporter protein increased by the forced expression of the MAGE-D1 gene.

48 hours after the addition of the MG132 (10, 50 or 100 µM) to the medium of the cell line constitutively expressing the SERT gene (indicated as "control" in FIG. 9), (in FIG. 9, "0" means no addition), the SERT protein signal with a high molecular weight (100 kD or more) was found by Western blotting under the same conditions as in the A (5) using the anti-SERT antibody (the lane of "Control 100" in the upper part of FIG. 9). The further increase of the high molecular weight SERT protein signal was found by forced expression of the MAGE-D1 gene (indicated with "MAGE-D1" in FIG. 9) (the lane of "MAGE-D1 100" in the upper part of FIG. 9). For the purpose of identifying the high molecular weight SERT protein signal, the ubiquitinated protein was isolated using the UBIQAPTURE-Q kit according to the procedure of the A (6), and analyzed by Western blotting using the anti-SERT antibody. As a result of this, the high molecular weight SERT protein signal was identified as the ubiquitinated SERT protein (the lanes of "Control 100" and "MAGE-D1 100" in the middle part of FIG. 9). It was suggested that the SERT protein is ubiquitinated, and degradated by proteasome, and the process is accelerated by the MAGE-D1.

Example 6

The Expression Amount of the Ubiquitinated Serotonin Transporter in the Established Lymphocytes Derived from the Patients with Depression, and Change in the Expression Amount of the Serotonin Transporter Caused by Proteasome Inhibitor The ubiquitinated serotonin transporter protein was identified by the band (76 kD) which was detected by Western blotting using the antibody to the serotonin transporter protein from the ubiquitinated protein isolated by immunoprecipitation using the UBIQAPTURE-Q kit. In comparison with the expression amount of the ubiquitinated serotonin transporter (the expression amount is regarded as the control of the amount of the ubiquitinated serotonin transporter protein) in the established lymphocytes derived from the healthy subject, that in the patient with depression who was effectively treated with the fluvoxamine antidepressant was 84.7% and had no significant difference, while that in the patients with depression to whom the antidepressant was not effective was 58.7% and significantly lower (FIG. 10a).

The MG132 was added to the cell culture medium used for subcultivation to make the final concentration of 20 µM, and 4 hours after that, the MG132 was added to the passage culture media of the established lymphocytes according to the procedure for recovering the established lymphocytes. In the test including the addition of the MG132, the expression amount of the ubiquitinated serotonin transporter in the established lymphocytes derived from the healthy subjects was 130.6%. In this test, in comparison with the expression amount of the ubiquitinated serotonin transporter in the established lymphocytes derived from the healthy subjects, the expression amount in the patients with depression to whom the antidepressant fluvoxamine was effective was 103.4% and had no significant difference, while the expression amount was 88.5% and significantly lower in the patients with depression to whom the antidepressant was not effective (FIG. 10a).

Figure 10:
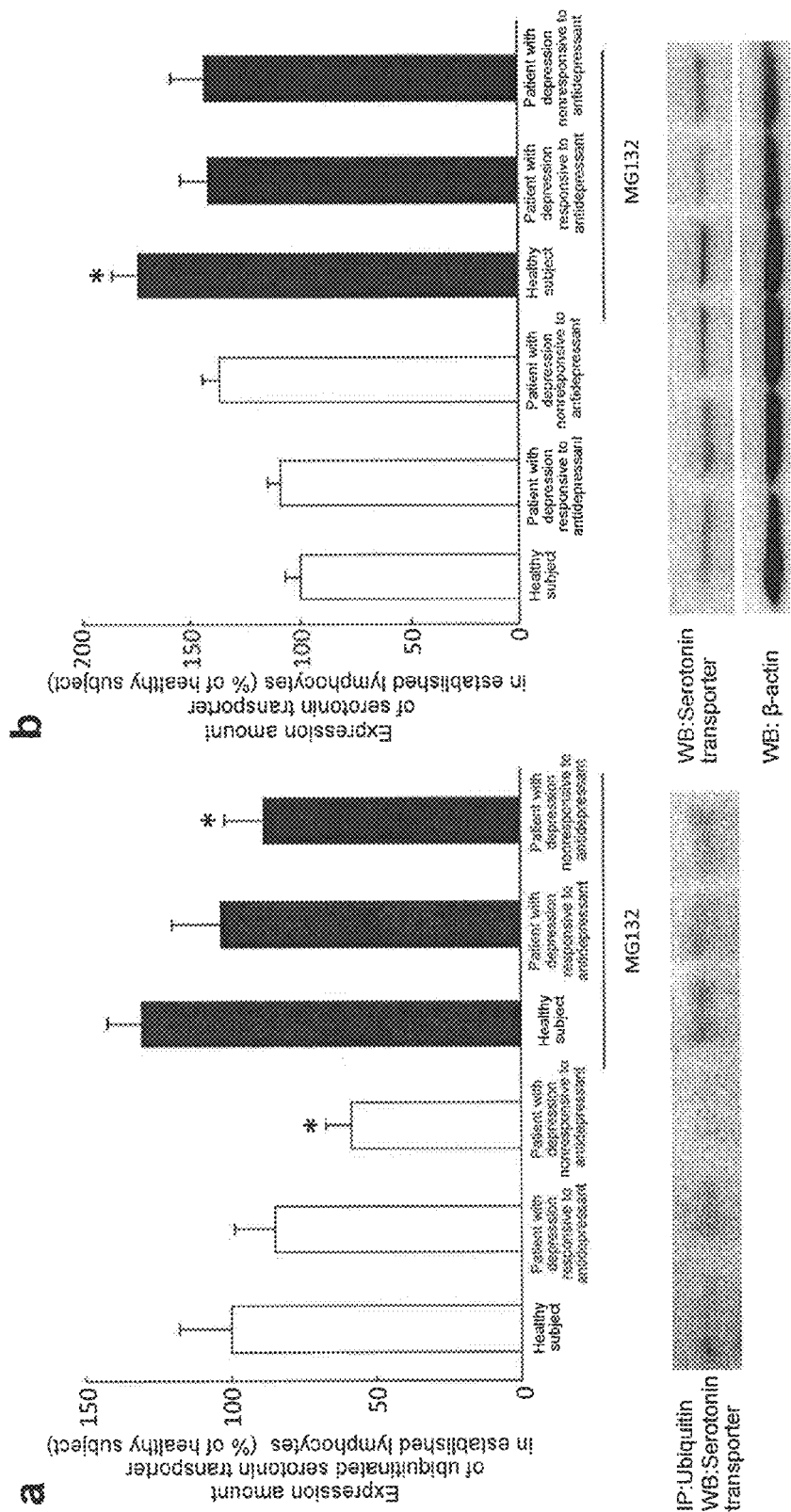
FIG. 10 shows the result of the measurement of the expression amount of the serotonin transporter and the amount of the ubiquitinated serotonin transporter protein in the established lymphocytes derived from the healthy subject and patient with depression.

In comparison with the expression amount of the serotonin transporter in the established lymphocytes derived from the healthy subjects (the expression amount is used as the control of the amount of the serotonin transporter protein), that amount significantly increased to 173.8% in the established lymphocytes containing the MG132 (FIG. 10b). The amount of the expression of the serotonin transporter in the established lymphocytes derived from the patients with depression to whom the antidepressant was effective was 109.5%, and that in the established lymphocytes containing the MG132 was 141.9% (FIG. 10b). The amount of the expression of the serotonin transporter in the established lymphocytes derived from the patients with depression to whom the antidepressant was not effective was 136.9%, and 143.6% in the established lymphocytes containing the MG132 (FIG. 10b). Regardless of the presence or absence of the effect of the antidepressant, in the established lymphocytes of the patients with depression, the addition of the MG132 did not significantly increase the expression amount of the serotonin transporter. The above studies were carried out six times, and the results were recorded as averages.

These results indicate that the expression amount of the ubiquitinated serotonin transporter decreased in the established lymphocytes derived from the antidepressant-nonresponsive patients. It is considered that as a result of the decrease in the degradation of the serotonin transporter by protease through ubiquitination, the increase in the expression amount of the serotonin transporter in response to the protease inhibitor was not found in the established lymphocytes derived from the patients with depression.

The proportion of the amount of the ubiquitinated SERT protein to the whole amount of the SERT protein (the amount of the ubiquitinated SERT protein/whole amount of the SERT protein) calculated based on the measurement result of the test without the addition of the MG132 was 72.1% in the established lymphocytes derived from the antidepressant-responsive patients with depression, and 39.2% in the established lymphocytes derived from the antidepressant-nonresponsive patients, in comparison with the established lymphocytes derived from healthy subjects (the proportion of the amount of the ubiquitinated SERT protein to the whole amount of the SERT protein calculated from the established lymphocytes derived from the healthy subject is used as the control). The proportion of the ubiquitinated serotonin transporter protein in the established lymphocytes derived from the patients with depression was at a low level in comparison with that proportion in the healthy subjects.

The significance test in these experiments used one way layout analysis of variance and the Fisher's PLSD method, which is a post-hoc analysis method.

In Example 6, "the whole amount of SERT protein" means the whole amount of the SERT protein detected using the antibody, and includes the amount of the ubiquitinated SERT protein.

The serotonin transporter is likely ubiquitinated, and degradated by proteasome.

The influence of the inhibition of the degradation of the serotonin transporter was studied by the addition of the MG-132, which is a proteasome inhibitor. The expression of the serotonin transporter in the healthy subjects was increased by the addition of the MG-132 (FIG. 10b). On the other hand, the expression of the serotonin transporter in the patients with depression responsive or nonresponsive to the antidepressant was not changed by the addition of the MG-132 (FIG. 10b).

The expression of the ubiquitinated serotonin transporter in the patients with depression nonresponsive to the antidepressant was significantly lower than that in the healthy subjects (FIG. 10a). This change was also found by the addition of the MG-132 (FIG. 10a).

If the serotonin transporter is not ubiquitinated, an excessive amount of serotonin transporter is present in the body, so that the amount of the serotonin in the synaptic cleft becomes deficient, which likely causes depression. Accordingly, it is considered that the less the increase of the expression of the serotonin transporter by the addition of the MG-132, or the lower the proportion of the ubiquitinated serotonin transporter, the higher the possibility of having depression.

From the above facts, the quantitation of the ubiquitinated serotonin transporter contained in the lymphocytes, platelets, and the blood containing them, and the change in the amount of the serotonin transporter by a protease inhibitor are useful as the methods for determining depression.

INDUSTRIAL APPLICABILITY

The present invention provides a method for utilizing a useful novel marker and a kit for analyzing the ubiquitinated serotonin transporter.

The invention claimed is:

1. A method for determining depression,
wherein an amount of a serotonin transporter including an amount of an ubiquitinated serotonin transporter in a blood sample treated with a proteasome inhibitor is defined as an amount of an inhibitor-treated serotonin transporter, and an amount of a serotonin transporter in an untreated blood sample is defined as an amount of an untreated serotonin transporter,
the method comprising:
a step of analyzing the amount of the inhibitor-treated serotonin transporter and the amount of the untreated serotonin transporter in a blood sample collected from a subject;
a step of comparing the difference between the amount of the untreated serotonin transporter and the amount of the inhibitor-treated serotonin transporter obtained from the blood sample collected from the subject (the difference between the untreated and inhibitor-treated amounts), and the difference between the untreated and inhibitor-treated amounts obtained from blood sampling of one or more healthy subjects; and
a step of determining that the subject has depression when the difference between the untreated and inhibitor-treated amounts obtained from the blood sample collected from the subject is smaller than the difference between the untreated and inhibitor-treated amounts obtained from the blood sampling of the one or more healthy subjects.

2. A method for determining depression,
wherein an amount of a serotonin transporter including an amount of an ubiquitinated serotonin transporter in a blood sample treated with a proteasome inhibitor is defined as an amount of an inhibitor-treated serotonin transporter,
the method comprising:
a step of analyzing the amount of the inhibitor-treated serotonin transporter in a blood sample collected from a subject;
a step of comparing the difference between the amount of the inhibitor-treated serotonin transporter obtained from the blood sample collected from the subject and the amount of the inhibitor-treated serotonin transporter obtained from blood sampling of one or more healthy subjects; and
a step of determining that the subject has depression when the amount of the inhibitor-treated serotonin transporter obtained from the blood sample collected from the subject is smaller than the amount of the inhibitor-treated serotonin transporter obtained from the blood sampling of the one or more healthy subjects.

3. A method for determining depression,
wherein an amount of a serotonin transporter including an amount of an ubiquitinated serotonin transporter in a blood sample treated with a proteasome inhibitor is defined as an amount of an inhibitor-treated serotonin transporter, and an amount of a serotonin transporter in an untreated blood sample is defined as an amount of an untreated serotonin transporter,
the method comprising:
a step of analyzing the amount of the inhibitor-treated serotonin transporter and the amount of the untreated serotonin transporter in a blood sample collected from a subject; and
a step of determining that the subject has depression when the amount of the inhibitor-treated serotonin transporter obtained from the blood sample collected from the subject is 1.7 times or less the amount of the untreated serotonin transporter.

4. The method of claim 1, further comprising a step of analyzing the amount of the inhibitor-treated serotonin transporter and the amount of the untreated serotonin transporter in blood sampling of one or more healthy subjects as to provide the untreated and inhibitor-treated amounts of the healthy subject used in the step of comparing.

5. The method of claim 1, wherein the difference between healthy subject untreated and inhibitor-treated amounts used in the steps of comparing and determining is based on an average of untreated and inhibitor-treated amounts obtained from blood sampling of a plurality of healthy subjects.

6. The method of claim 2, further comprising a step of analyzing the amount of the inhibitor-treated serotonin transporter in blood sampling of one or more healthy subjects as to provide the amount of the inhibitor-treated serotonin transporter of the healthy subject used in the step of comparing.

7. The method of claim 2, wherein the amount of the inhibitor-treated serotonin transporter of the healthy subject used in the steps of comparing and determining is based on an average of inhibitor-treated serotonin transporter amounts obtained from blood sampling of a plurality of healthy subjects.

\* \* \* \* \*